(12) United States Patent
Boyle et al.

(10) Patent No.: US 10,531,890 B2
(45) Date of Patent: Jan. 14, 2020

(54) SCORING BALLOON WITH TRANSLATING SCORING WIRES

(71) Applicant: C.R. Bard, Inc., Tempe, AZ (US)

(72) Inventors: Melissa Boyle, Phoenix, AZ (US); Mark Nicholas Wright, Gilbert, AZ (US)

(73) Assignee: C.R. BARD, INC., Tempe, AZ (US)

( * ) Notice: Subject to any disclaimer, the term of this patent is extended or adjusted under 35 U.S.C. 154(b) by 59 days.

(21) Appl. No.: 15/395,901

(22) Filed: Dec. 30, 2016

(65) Prior Publication Data

US 2018/0185051 A1 Jul. 5, 2018

(51) Int. Cl.
| | | |
|---|---|---|
| *A61B 17/3207* | (2006.01) | |
| *A61B 17/32* | (2006.01) | |
| *A61B 17/00* | (2006.01) | |
| *A61M 25/09* | (2006.01) | |

(52) U.S. Cl.
CPC ......... *A61B 17/320725* (2013.01); *A61B 17/320068* (2013.01); *A61B 2017/00398* (2013.01); *A61B 2017/00402* (2013.01); *A61B 2017/00867* (2013.01); *A61B 2017/00889* (2013.01); *A61B 2017/00893* (2013.01); *A61B 2017/320008* (2013.01); *A61B 2017/320089* (2017.08); *A61M 25/09* (2013.01)

(58) Field of Classification Search
CPC .... A61M 2025/1086; A61M 2025/109; A61M 2025/1093; A61M 25/104; A61B 17/320725; A61B 17/3207; A61B 2017/22051; A61B 2017/22081
See application file for complete search history.

(56) References Cited

U.S. PATENT DOCUMENTS

| | | | | |
|---|---|---|---|---|
| 5,395,332 A | * | 3/1995 | Ressemann | A61M 25/0068 600/585 |
| 5,546,948 A | * | 8/1996 | Hamm | A61B 5/6848 600/463 |
| 5,628,746 A | * | 5/1997 | Clayman | A61B 18/08 606/159 |
| 5,904,679 A | * | 5/1999 | Clayman | A61B 17/22 604/114 |
| 6,394,995 B1 | | 5/2002 | Solar et al. | |
| 7,901,378 B2 | | 3/2011 | Solar et al. | |
| 8,070,729 B2 | | 12/2011 | Solar et al. | |

(Continued)

OTHER PUBLICATIONS

International Patent Application Serial No. PCT/US16/59537 as filed.

*Primary Examiner* — Sarah A Simpson
(74) *Attorney, Agent, or Firm* — King & Schickli, PLLC

(57) ABSTRACT

A device for introduction into a body vessel includes a shaft, a balloon positioned at the distal end of the shaft, a guidewire disposed longitudinally within the shaft to receive a guidewire during use, a balloon disposed at the distal end of the shaft, and longitudinal scoring wires to score a vascular lesion attached to the distal end of the shaft. The scoring wires are disposed over the balloon and disposed within the shaft. The proximal ends are welded or otherwise affixed to a spring mounted in the handle. The balloon expands when fluid is delivered to the balloon through the inflation lumen. This expansion pushes the scoring wires against the vascular lesion. The scoring wires attach to a source of vibrations. The scoring wires are made of a helical coil.

8 Claims, 15 Drawing Sheets

(56) References Cited

U.S. PATENT DOCUMENTS

| | | |
|---|---|---|
| 8,262,621 B2 | 9/2012 | Solar et al. |
| 8,486,025 B2 | 7/2013 | Solar et al. |
| 8,685,049 B2 | 4/2014 | Schur et al. |
| 8,685,050 B2 | 4/2014 | Schur et al. |
| 8,702,736 B2 | 4/2014 | Schur et al. |
| 9,050,437 B2 | 6/2015 | Shaked et al. |
| 9,282,991 B2 | 3/2016 | Schur et al. |
| 9,504,473 B2 | 11/2016 | Shaked et al. |
| 9,532,798 B2 | 1/2017 | Schur et al. |
| 2005/0154440 A1* | 7/2005 | Limon ............... A61F 2/958 623/1.11 |
| 2008/0082050 A1 | 4/2008 | Solar et al. |
| 2009/0275920 A1 | 11/2009 | Solar et al. |
| 2011/0118774 A1 | 5/2011 | Solar et al. |
| 2014/0277002 A1* | 9/2014 | Grace ............... A61B 17/22 606/159 |
| 2015/0343191 A1* | 12/2015 | Spano ............ A61B 17/22012 604/22 |
| 2017/0119428 A1* | 5/2017 | Boyle ............ A61B 17/22012 |
| 2017/0119460 A1* | 5/2017 | Smith ............. A61B 18/1492 |

* cited by examiner

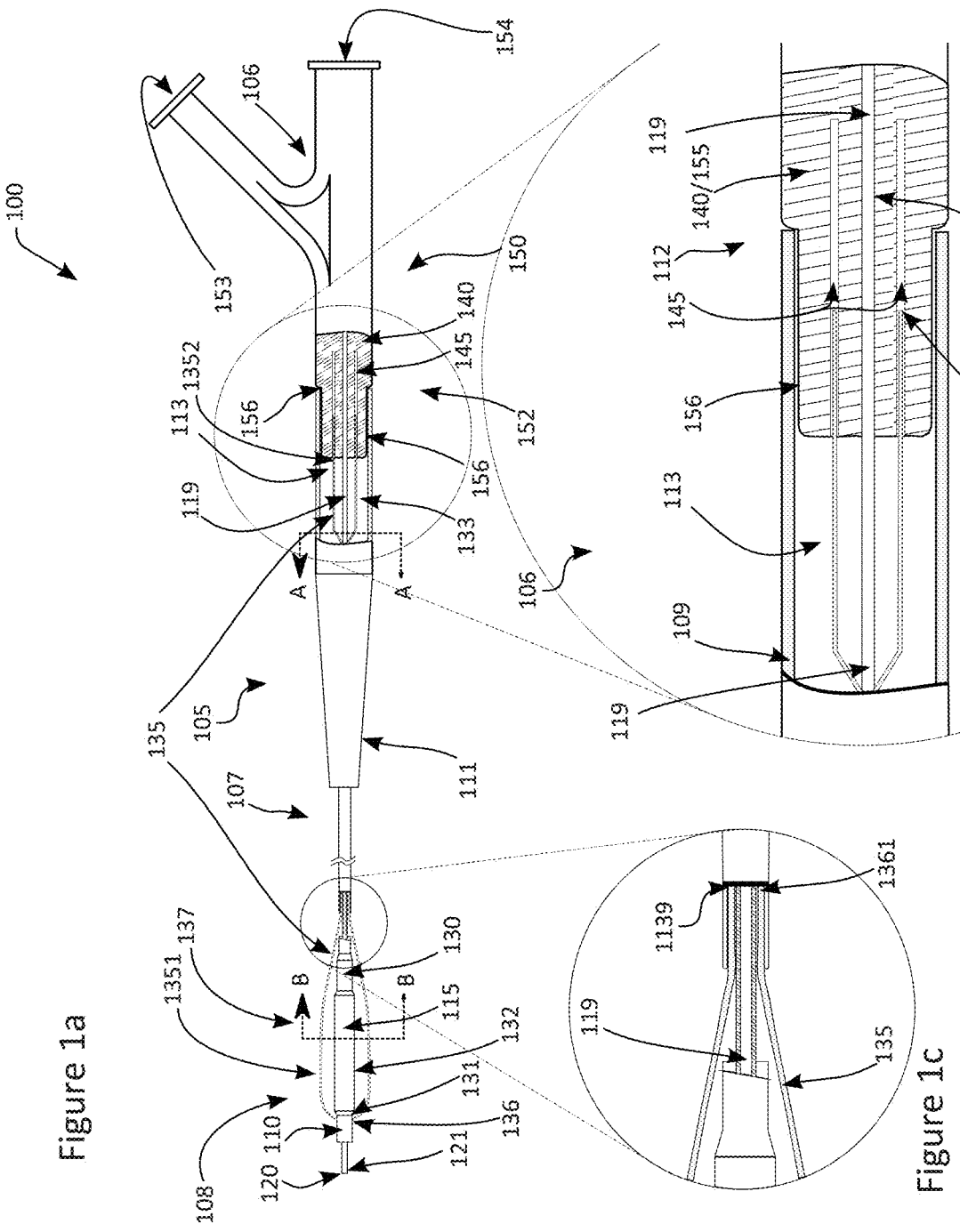

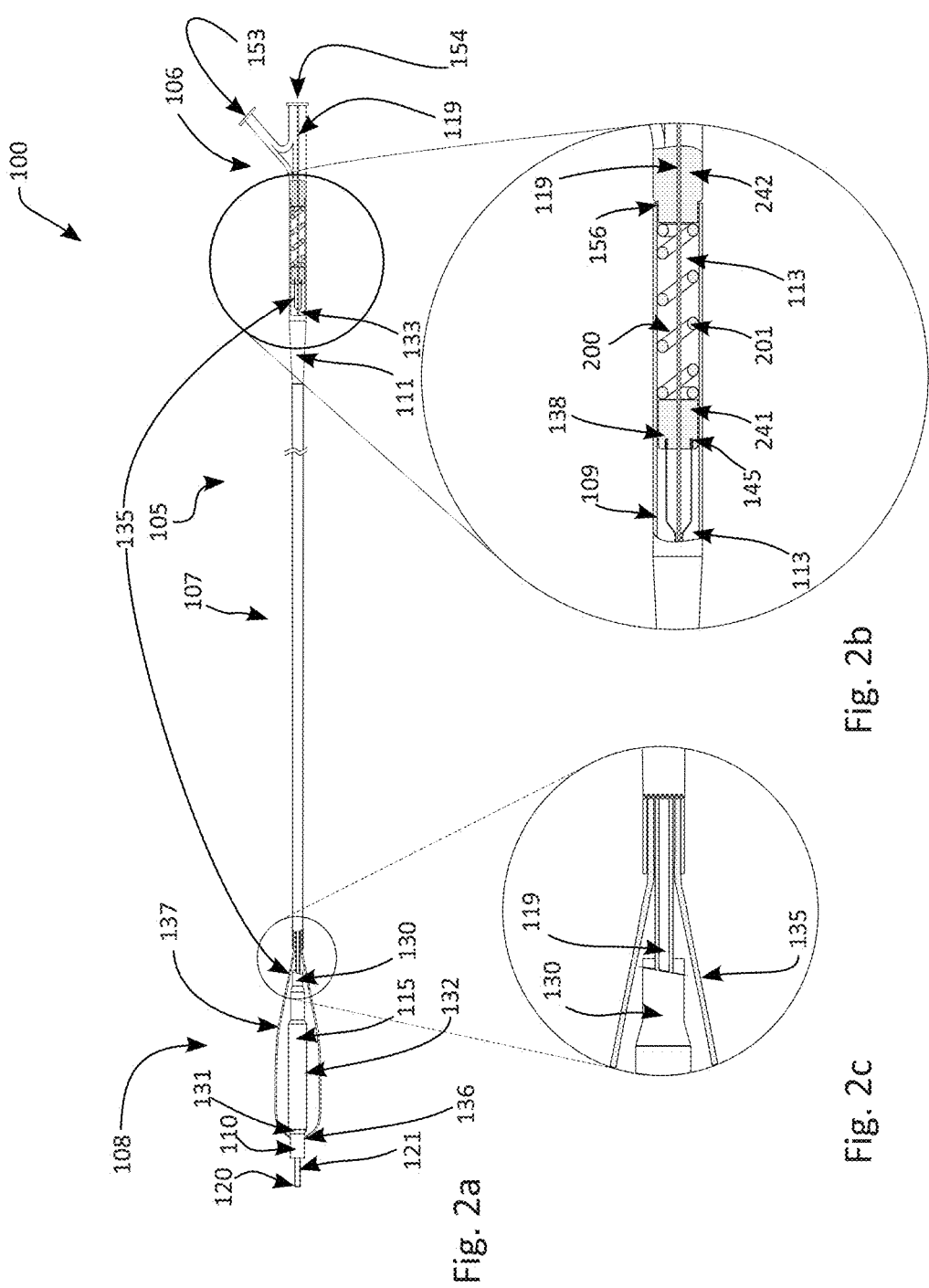

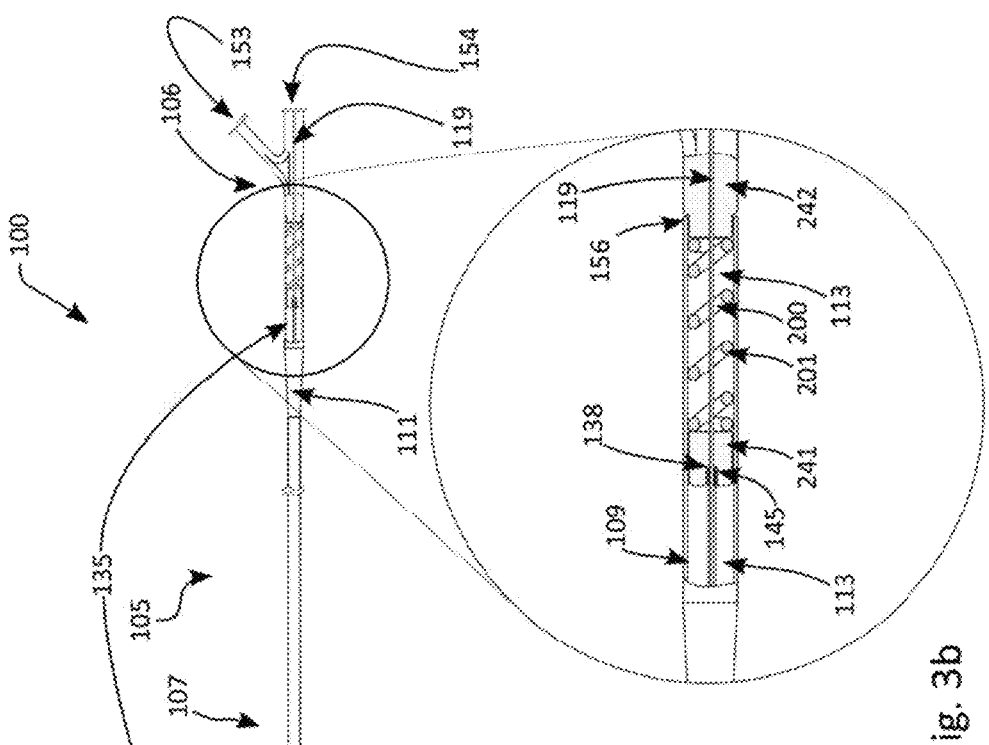
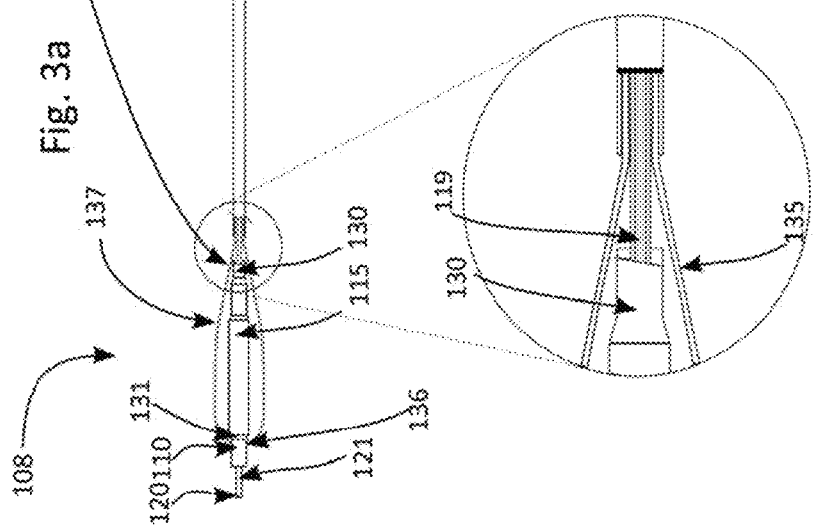
Fig. 3a
Fig. 3b
Fig. 3c

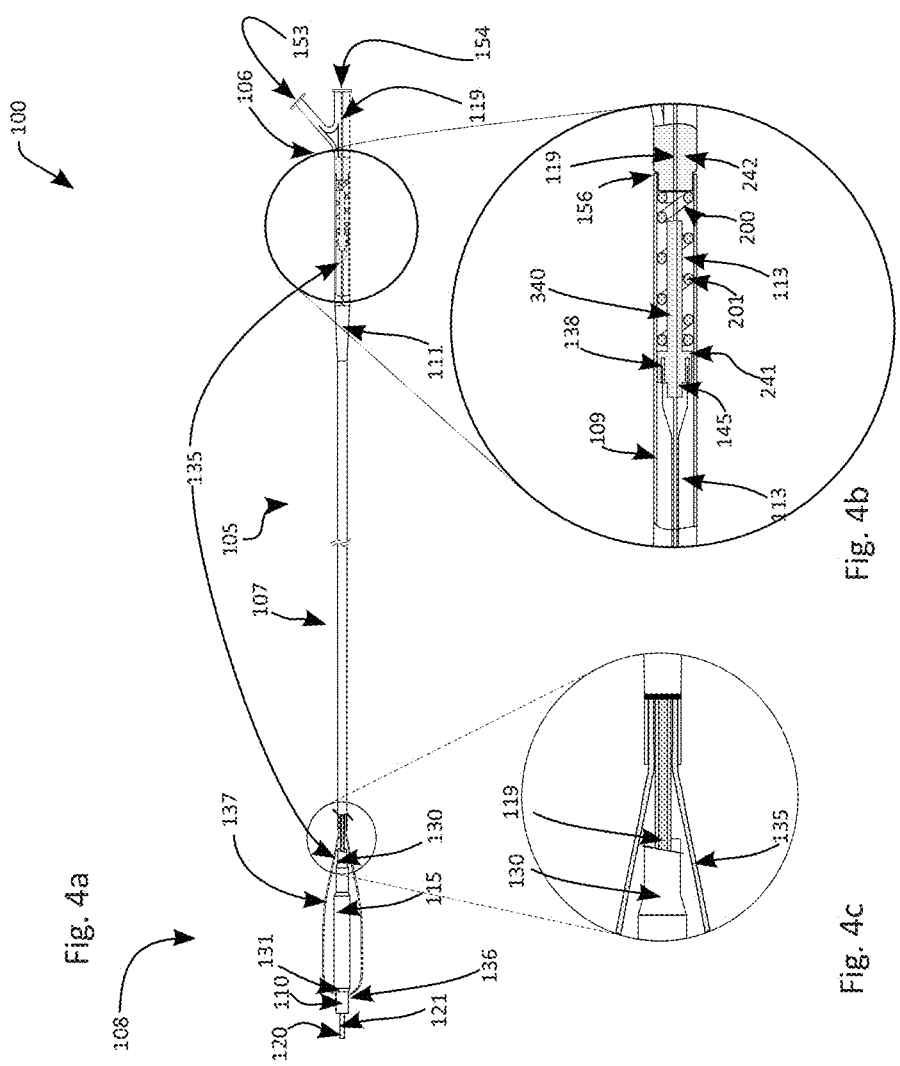

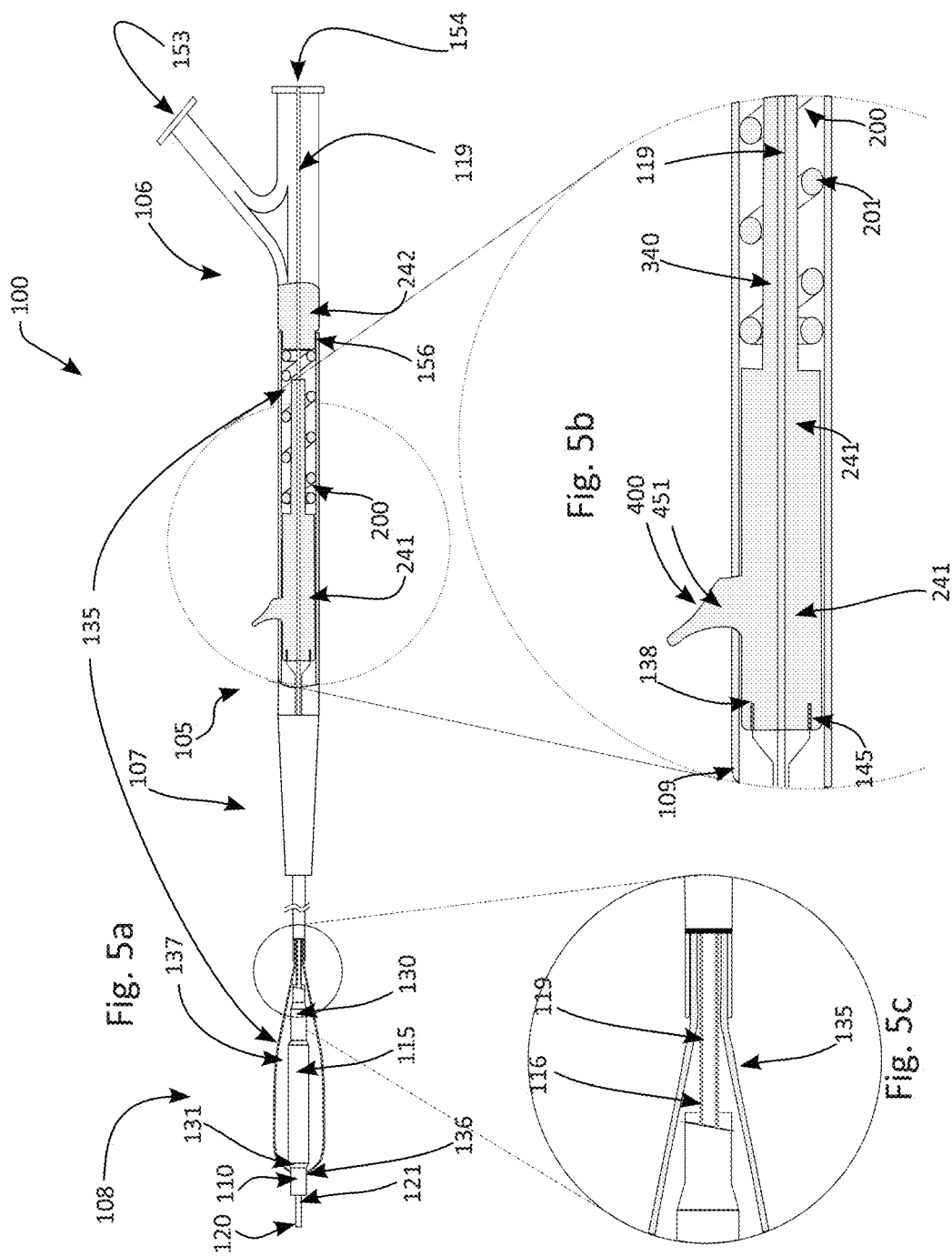

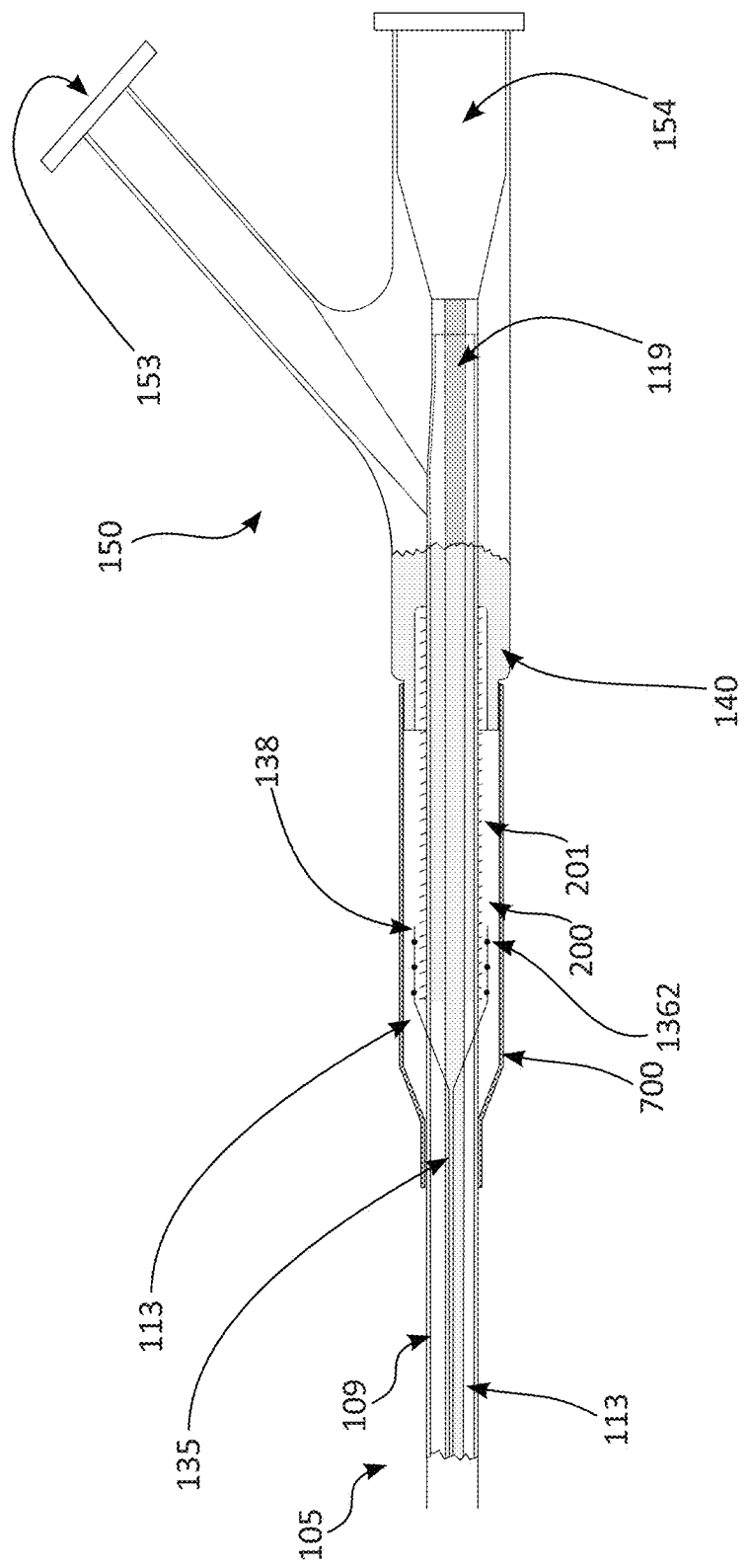

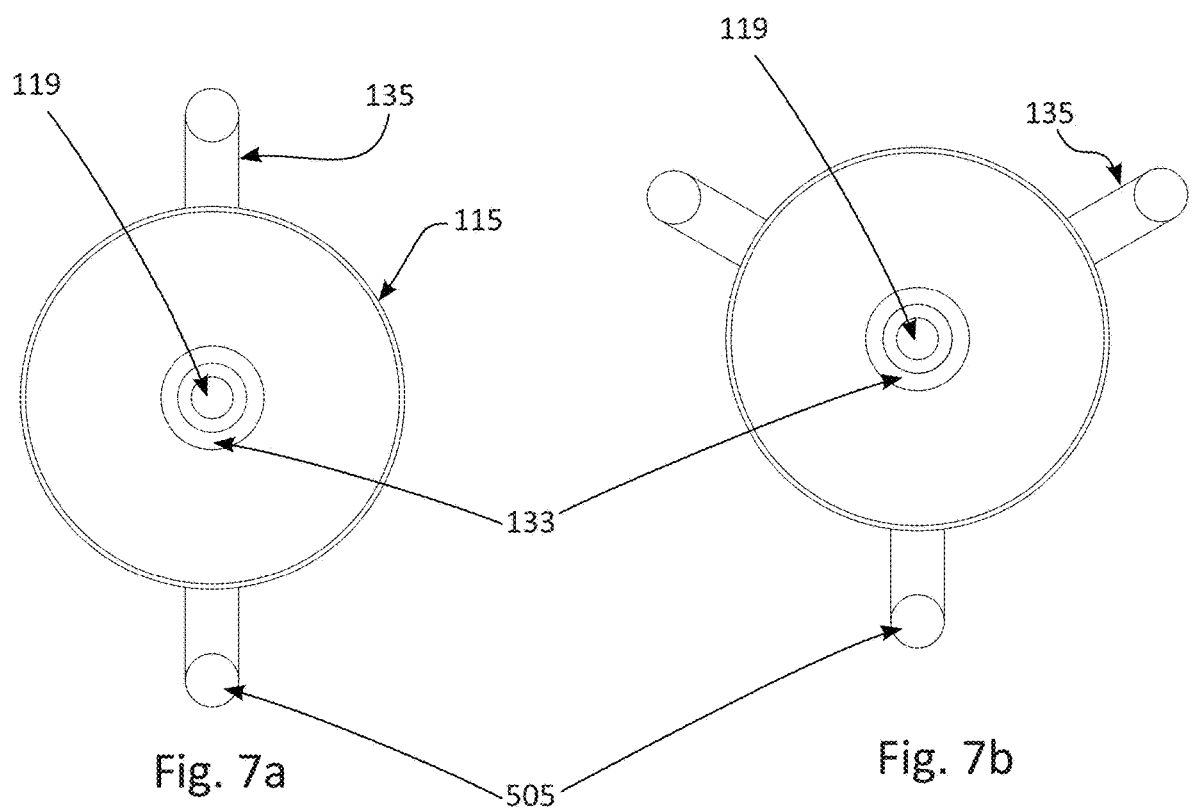

SCORING BALLOON WITH TRANSLATING SCORING WIRES

BACKGROUND OF THE INVENTION

Balloon dilatation catheters are used to treat lesions in vessels. However, difficulties are encountered in navigating tortuous anatomy and safely crossing very tight lesions. Moreover, some lesions are difficult to dilate using just a balloon, and require a focused force to dilate the lesion at safe inflation pressures.

U.S. Pat. No. 6,394,995 to Solar et al. describes a system used to provide enhanced force to treat a lesion. This system has a flexible advancement member with a tracking member slidable over a guidewire, and a balloon having a distal end attached to the tracking member. But this type of system provides limited focused force and lacks pushability and maneuverability.

SUMMARY OF THE INVENTION

The present invention provides a scoring balloon catheter that can be used for treating vascular lesions. In use, the balloon presses scoring wires into the lesion. The catheter includes a shaft having a distal region and a lumen; an inflatable balloon mounted on the distal region; a scoring wire mounted to the shaft distally of the distal end of the balloon and extending proximally past the proximal end of the balloon; and a vibrating means connected to the scoring wire for vibrating the scoring wire. The vibrating means can be any means as known to those of ordinary skill in the art. In some embodiments, the vibrating means includes motors, micro motors, solenoids, piezoelectrics, etc.

In these or other embodiments, the scoring wires have a proximal end disposed within a hub mounted in the shaft proximally of the balloon, on the proximal-most half of the shaft, or on the proximal end of the shaft.

In these or other embodiments, a transmission member is disposed between the vibrating means and scoring wires. The transmission member has a driven end and transmitting end wherein the transmitting end contacts the hub or the proximal end of the scoring wire. In other embodiments, the vibrating means is disposed completely inside the catheter.

In these or other embodiments, the transmission member extends through the wall of the shaft. In other embodiments, the transmission member extends into a proximal end of the catheter. And depending on the embodiment, the vibrating means imparts longitudinal motion to the scoring wire or the vibrating means imparts axial motion to the scoring wire.

The present invention provides a scoring balloon catheter that can be used for treating vascular lesions. In use, the balloon presses scoring wires into the lesion. The catheter includes a shaft having a distal region and a lumen; an inflatable balloon mounted on the distal region; a scoring wire mounted to the shaft distally of the distal end of the balloon and extending proximally past the proximal end of the balloon having a fixed end mounted on the shaft between a shaft distal end and the balloon. A longitudinally movable end of the scoring wire associated with a hub or spring; and an intermediate portion of the scoring wire running alongside of a working region of the balloon. The scoring wire may comprise a helical coil section in these embodiments. The diameter of the helical coil ranges from 0.009" to 0.013", and the diameter of the wire for the coil ranges from 0.005" to 0.010".

In some embodiments, the helical coil section begins at the fixed end of the scoring wire and ends at the proximal end of the intermediate portion of the scoring wire. In some other embodiments, the helical coil section begins at the distal end of the intermediate portion of the scoring wire and ends at the proximal end of the intermediate portion of the scoring wire. The helical coil section exhibits spring-like elasticity in the longitudinal direction and in the axial direction.

BRIEF DESCRIPTION OF THE DRAWINGS

The above and further advantages of the present invention may be better understood by referring to the following description in conjunction with the accompanying drawings in which:

FIG. 1a is a front view of an example of an invention device.

FIG. 1b is a magnified view of the indicated portion of FIG. 1a.

FIG. 1c is a magnified view of the indicated portion of FIG. 1a.

FIG. 2a is a front view of another example of an invention device.

FIG. 2b is a magnified view of the indicated portion of FIG. 2a.

FIG. 2c is a magnified view of the indicated portion of FIG. 2a.

FIG. 3a is a front view of another example of an invention device.

FIG. 3b is a magnified view of the indicated portion of FIG. 3a.

FIG. 3c is a magnified view of the indicated portion of FIG. 3a.

FIG. 4a is a front view of another example of an invention device.

FIG. 4b is a magnified view of the indicated portion of FIG. 4a.

FIG. 4c is a magnified view of the indicated portion of FIG. 4a.

FIG. 5a is a front view of another example of an invention device.

FIG. 5b is a magnified view of the indicated portion of FIG. 5a.

FIG. 5c is a magnified view of the indicated portion of FIG. 5a.

FIG. 6 is a front view of another embodiment of an invention device.

FIG. 7a is an end view showing the embodiment of FIG. 1 at section plane AA.

FIG. 7b is similar to FIG. 7a viewing section plane AA on a different invention embodiment.

Figure 8A:
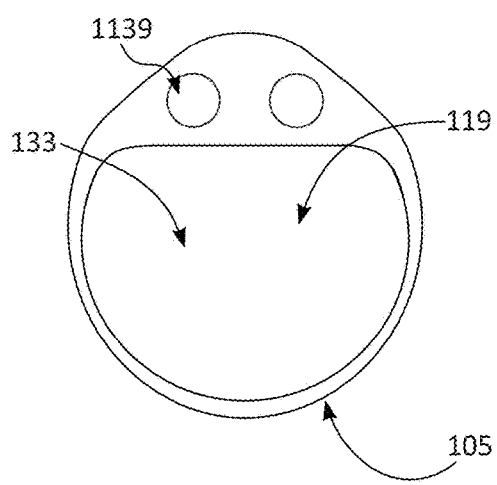
FIG. 8a is an end view showing an embodiment of the device taken along a section plane similar to section plane BB.

The drawings are not necessarily drawn proportionally or to scale. For example, the dimensions of some of the elements may be exaggerated relative to other elements for clarity or several physical components may be included in one functional block or element. Further, sometimes reference numerals may be repeated among the drawings to indicate corresponding or analogous elements.

DETAILED DESCRIPTION

In the following detailed description, numerous specific details are set forth to provide a thorough understanding of the present invention. Those of ordinary skill in the art will know that the present invention may be practiced without these specific details. In other instances, well-known methods, procedures, components, or structures may not have been described in detail so as not to obscure the present invention.

The present invention is directed to systems and methods for treatment of a vessel. The principles and operation of systems and methods of the present invention may be better understood with reference to the drawings and accompanying descriptions.

The invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein are for the purpose of description and should not be regarded as limiting.

Certain features of the invention that are, for clarity, described in the context of separate embodiments, may also be provided in combination in a single embodiment. Conversely, various features of the invention that are, for brevity, described in the context of a single embodiment, may also be provided separately or in any suitable sub-combination.

Table of components.

| | |
|---|---|
| 100 | scoring balloon (SCB) catheter |
| 105 | shaft |
| 106 | shaft proximal section |
| 107 | shaft middle section |
| 108 | shaft distal section |
| 109 | shaft wall |
| 110 | shaft distal end |
| 111 | shaft tapered section |
| 112 | shaft proximal end |
| 113 | shaft lumen |
| 115 | inflatable balloon (IB) |
| 119 | guidewire lumen (GWL) |
| 120 | GWL distal end |
| 121 | GWL outer surface |
| 130 | IB proximal end |
| 131 | IB distal end |
| 132 | IB outer surface |
| 133 | IB lumen |
| 135 | scoring wire (SCW) |
| 1351 | SCW distal section |
| 1352 | SCW proximal section |
| 136 | fixed SCW end |
| 1362 | weld joint |
| 137 | SCW IB section |
| 138 | moveable SCW end |
| 1139 | SCW lumen |
| 140 | hub |
| 141 | GWL passage |
| 145 | hub lumen |

Table of components.—continued

| | |
|---|---|
| 150 | handle assembly (HA) |
| 152 | transmission sub-assembly |
| 153 | HA IB lumen port |
| 154 | HA GW port |
| 155 | HA distal end portion |
| 156 | HA stepped-down portion |
| 200 | spring |
| 201 | spring wire |
| 241 | hub distal section |
| 242 | hub proximal section |
| 340 | narrowed region |
| 400 | fingergrip |
| 451 | extension |
| 505 | SCW cross-section |
| 610 | see IBL |
| 700 | hub cover |
| 1000 | catheter |
| 1100 | catheter |
| 1110 | internal hub |
| 1115 | vibration means |
| 1120 | transmission member |
| 1300 | catheter |
| 1310 | vibrating hub |
| 1315 | vibration means |
| 1400 | catheter |
| 1500 | catheter |
| 1535 | coiled scoring wire |

Definitions

"fixed"—inseparable within the operational environment of the device.

"operational environment"—any environment in which the device would conceivably operate as an intravascular balloon catheter.

"longitudinally resilient"—the ability to repeatedly move longitudinally.

"mechanically communicating"—describes the ability of one object to connect sufficiently such that its movement causes another object to move and vice versa.

"rail"—a substantially longitudinal object that supports and guides the movement of another object.

"slidably engaged" component—a component that fits into a passageway or around a rail such that the component is largely or substantially constrained in two dimensions. Instead of the third dimension constraining the component, the component is unconstrained to some degree allowing the component to move longitudinally a substantial distance within the passageway or along the rail. If the system has stops or other components that curtail longitudinal movement, but still permit substantial longitudinal motion, the component is considered slidably engaged.

"effectively engaged"—a scoring wire is effectively engaged when it engages the lesion well enough for the treatment to substantially affect the lesion.

Invention catheters can be over-the-wire, short rapid exchange, or rapid exchange platform. If the catheter is a short rapid exchange platform, an inner member may traverse the entire length of the catheter.

Turning to the invention embodiments, FIG. 1a depicts an embodiment of the invention device. In this invention embodiment, a scoring balloon (SCB) catheter 100 is shown in a front view with selected sections shown in a magnified view. SCB catheter 100 comprises components as discussed below. For instance, catheter 100 comprises shaft 105. Shaft 105 has shaft proximal section 106 connected to shaft middle section 107 and shaft middle section 107 connected to shaft distal section 108. Shaft tapered section 111 joins shaft proximal section 106 to shaft middle section 107. Shaft 105 also comprises shaft wall 109, which provides a degree of rigidity to shaft 105 such that shaft 105 is suitable (as judged by those of ordinary skill in the art) for tracking into vasculature or tortuous vasculature being neither too rigid or too flexible. In some embodiments, the rigidity or flexibility is modified by adding a longitudinal member (not shown) to SCB catheter 100. Shaft 105 comprises Pebax, in some embodiments.

In some embodiments, shaft tapered section 111 is fixed to shaft middle section 107. In some embodiments, shaft wall 109 ends before shaft distal end 110 ends.

For purposes of this document, shaft distal end 110 is the end of shaft 105 that enters the patient first. Similarly, any other "distal"-characterized component means the component portion closer to shaft distal end 110 then is any other component portion. Likewise, any "proximal"-characterized component means the component portion further from shaft distal end 110 then is any other component portion.

SCB catheter 100 further comprises inflatable balloon (IB) 115. Inflatable balloon 115 mounts to shaft 105 within shaft distal section 108. In some embodiments, inflatable balloon 115 ends at shaft distal end 110. In these or other embodiments, inflatable balloon 115 is fixed to shaft 105.

Inflatable balloon 115 comprises IB proximal end 130 and IB distal end 131. A typical embodiment has a flexible, polymeric film serving as inflatable balloon 115. IB outer surface 132 ends up facing abluminally after inflatable balloon 115 mounts to shaft 105. For this disclosure, IB proximal end 130 is the portion of inflatable balloon 115 that attaches or fixes the proximal end of inflatable balloon 115 to shaft 105. IB proximal end 130 is defined as the proximal portion of inflatable balloon 115 that remains contacting shaft 105 after inflatable balloon 115 is inflated.

For this disclosure, IB distal end 131 is the portion of inflatable balloon 115 that distally attaches or fixes inflatable balloon 115 to shaft 105. IB distal end 131 is defined as the distal portion of inflatable balloon 115 that remains contacting shaft 105 after inflatable balloon 115 in inflated.

IB lumen 133 fluidly communicates with inflatable balloon 115, which allows inflatable balloon 115 to be inflated by fluid passing through IB lumen 133.

SCB catheter 100 further comprises guidewire lumen (GWL) 119, which longitudinally extends at least from shaft proximal end 112 to flush with or beyond shaft distal end 110. GW lumen 119 ends at GWL distal end 120.

In some embodiments, IB proximal end 130 and IB distal end 131 connect to GWL outer surface 121 or shaft 105 using any method known to those of ordinary skill in the art.

SCB catheter 100 further comprises scoring wire (SCW) 135. Scoring wire 135 comprises fixed SCW end 136, SCW IB section 137, and movable SCW end 138. Fixed SCW end 136 connects within shaft distal section 108 distal of IB distal end 131. In some embodiments, fixed SCW end 136 attaches to GWL outer surface 121. In other embodiments, fixed SCW end 136 attaches to the outer side of shaft wall 109. Fixed SCW end 136 attaches using any method known to those of ordinary skill in the art.

This configuration provides for a focused force element (scoring wire 135) alongside inflatable balloon 115.

The distance between scoring wire 135 and IB outer surface 132 can be any value recognized as useful by those of ordinary skill in the art. Once proximally past inflatable balloon 115, scoring wire 135 dives below shaft wall 109, extending proximally inside of shaft 105. Movable SCW end 138 sits inside of shaft 105 within shaft proximal section 106. In some embodiments, scoring wire 135 occupies at least part of SCW lumen 1139 (shown in FIGS. 8a and 8b).

FIGS. 1a-FIG. 5b depicts SCB catheter 100 as having two scoring wires. In some embodiments, SCB catheter 100 has 1-15, 3-10, or 2-5 scoring wires. In some embodiments, the diameter of SCW 135 is between 0.003 inches and 0.040 inches, or 0.005 inches and 0.015 inches, 0.008 inches and 0.012 inches. In some embodiments, the diameter of SCW 135 is 0.10 inches. SCW 135 need not have a uniform diameter. In some embodiments, SCW distal section 1351 has a diameter larger than SCW proximal section 1352. In some embodiments, SCW distal section 1351 has a diameter smaller than SCW proximal section 1352. In some embodiments, SCW 135 comprises metals, metal alloys, polymers, and shape memory materials that are metal- or polymer-based.

SCB catheter 100 further comprises hub 140. Hub 140 resides inside of shaft 105 within shaft proximal section 106. Hub 140 comprises a GWL passage 141 for guidewire lumen 119 to pass through. Hub 140 further comprises one or more hub lumens 145 that interact with movable SCW end 138.

In some embodiments, the interaction encompasses movable SCW end 138 connected in or to hub lumen 145. In some embodiments, movable SCW end 138 is fixed to hub lumen 145. In other embodiments, the interaction encompasses movable SCW end 138 being slidably engaged inside of hub lumen 145. In some embodiments, hub 140 comprises any biocompatible material such as metals, metal alloys, and polymers. In some embodiments, hub 140 comprises nylon, Pebax, or any other suitable material known to those of ordinary skill in the art.

In some embodiments, hub 140 is substantially fixed inside shaft proximal section 106 with movable SCW end 138 slidably engaged or disposed within hub lumen 145. In some embodiments, hub 140 is longitudinally movable or elastic, allowing movable SCW end 138 to move longitudinally by pulling hub 140 distally, by moving hub 140 or by stretching material of hub 140. For instance, in some embodiments, hub 140 is elastic. When movable SCW end 138 is subjected to a distally directed force that causes it to move distally and when movable SCW end 138 is fixed to or within hub lumen 145, the movement stretches hub 140. The restoring force or force counter to that distal stretching (counterforce) tends to move movable SCW end 138 substantially back into place when the distally directed force is removed.

In some embodiments, hub 140 is biased by a spring 200. In some embodiments, spring 200 mounts distal to hub 140 and in some embodiments, spring 200 mounts proximal to hub 140.

SCW catheter 100 further comprises handle assembly (HA) 150. Handle assembly 150 associates with shaft proximal end 109. Handle assembly 150 comprises HA port sub-assembly and HA transition sub-assembly. HA port sub-assembly occupies at least part of the proximal end of handle assembly 150. And HA transition sub-assembly occupies at least part of the distal end of handle assembly 150. HA port sub-assembly relates to HA transition sub-assembly. In some embodiments, HA port sub-assembly connects to or is fixed to HA transition sub-assembly. In some embodiments, HA port sub-assembly and HA transition sub-assembly together form a monolithic object or a number of objects or monolithic objects split by a plane containing SCW catheter 100's longitudinal axis.

HA transition sub-assembly comprises HA stepped-down portion 156 located at the distal end of HA transition sub-assembly. In some embodiments, the distal end of HA transition sub-assembly and the distal end of handle assembly 150 are the same object.

HA stepped-down portion 156 is a portion of HA transition sub-assembly in which the overall outside dimension has a step transition decreasing to a smaller diameter, sized to engage shaft proximal end 112.

In some embodiments, transition sub-assembly 152 does not have HA stepped-down portion 156.

Shaft 105 relates to handle assembly 150 through shaft proximal end 112 and HA stepped-down portion 156. In some embodiments, shaft 105 connects to handle assembly 150. For example, shaft proximal end 112 can slide over HA stepped-down portion 156 and the components can be fixed such as by welding, fusing, gluing, etc. Or the friction fit between shaft proximal end 112 and HA transition sub-assembly 152 can be strong enough to fix the components together. In some embodiments lacking HA stepped-down portion 156, shaft proximal end 112 can connect to handle assembly 150 through a butt joint between shaft proximal end 112 and HA transition sub-assembly 152.

HA port sub-assembly comprises HA GW port 154, which occupies the proximal end of HA port sub-assembly. In some versions of handle assembly 150, HA GW port 154 points away or directly away from shaft distal end 110. HA GW port 154 allows access from outside of SCB catheter 100 into guidewire lumen 119. In some versions of handle assembly 150, HA port sub-assembly also comprises HA IB lumen port 153, which angles out from the longitudinal axis of SCB catheter 100 at any of a variety of angles recognized as useful to those of ordinary skill in the art. In some versions, HA IB lumen port 153 flows into the guidewire-port-guidewire-lumen region and in other embodiments flows to a separate lumen inside or outside (not shown) of guidewire lumen 119. HA IB lumen port 153 also allows access from outside of SCB catheter 100 into a passageway (guidewire lumen 119 or IB lumen 133 (IBL)) that carries gas or inflation fluid into inflatable balloon 115 to inflate it or carries gas or inflation fluid out of inflatable balloon 115 to deflate it.

Operationally, in the devices taught by the FIG. 1a embodiment, for treatment of calcified lesions, for example, a physician cuts through the patient's tissue until an appropriately sized vessel is revealed. The vessel must lead to the lesion site following a path that SCB catheter 100 can follow. In some embodiments, the location of the lesion site causes those of ordinary skill in the art to select a more or less flexible shaft 105 or SCB catheter 100.

The physician opens the vessel, inserts a guidewire into the vessel, and advances the guidewire through the patient's vasculature under ultrasound, magnetic resonance, fluoroscopic, or some other type of guidance. Once the physician places the guidewire at a satisfactory site, the physician threads the proximal end of the guidewire into GWL distal end 120, through guidewire lumen 119, and ultimately out of SCB catheter 100—through HA GW port 154. With the guidewire in place and installed in SCB catheter 100, the physician maneuvers SCB catheter 100 along the guidewire until inflatable balloon 115 reaches the desired position near the lesion site. Typically, this position will allow at least one scoring wire 135 to effectively engage the lesion. After that, the physician inflates inflatable balloon 115 until scoring wire 135 firmly presses into or cracks the lesion. Once lesion treatment with SCB catheter 100 is complete, the physician deflates inflatable balloon 115, which allows scoring wire 135 to relax away from the lesion and from the vessel wall.

Scoring wire 135 contacts the lesion as long as inflatable balloon 115 remains inflated. The inflation time corresponds to the time the physician chooses for scoring wire 135 to contact the lesion. Those of ordinary skill in the art use inflation times of 5 seconds to 5 minutes. Those of ordinary skill in the art look to the nature of the lesion in determining the appropriate inflation time and inflation speed.

An aspect of this invention includes the behavior of scoring wire 135 during balloon inflation and specifically includes the behavior of movable SCW end 138.

As inflatable balloon 115 inflates, scoring wire (or wires) 135 expands outwardly, placing scoring wire 135 under longitudinal tension. A component of the force vector caused by that longitudinal tension points proximally from fixed SCW end 136 and distally from movable SCW end 138. But fixed SCW end 136 is fixed to shaft 105 or GWL outer surface 121. Therefore, any movement of scoring wire 135 occurs at movable SCW end 138. Hub 140 constrains the movement of movable SCW end 138 allowing it to move longitudinally. This movement decreases the strain on inflatable balloon 115 helping to maintain its engineered shape and helping to avoid any kinking in the balloon's neck, which was sometimes seen in prior art devices having scoring wires substantially fixed at both ends.

When the physician deflates the balloon, the forces previously causing scoring wire 135 to expand disappear, allowing scoring wire 135 (and movable SCW end 138) to relax. Hub 140 constrains the relaxation of movable SCW end 138. Specifically, hub 140 guides movable SCW end 138 into an arrangement similar to the initial arrangement of movable SCW end 138 before balloon inflation. Hub 140's action helps regularize the inflation and deflation steps increasing their predictability.

Returning to FIG. 1a, FIG. 1a depicts the catheter as described above. The specific shaft 105 can be made by a variety of methods as known to those of ordinary skill in the art. The embodiment shown in FIG. 1a comprises shaft 105 coupled (attached, connected, joined) to handle assembly 150 through HA distal end portion 155 and HA stepped-down portion 156. HA stepped-down portion 156 occupies shaft lumen 113 and substantially seals shaft proximal end 112 from the atmosphere. In some embodiments, shaft proximal end 112 and HA distal end portion 155 are glued together with an adhesive. In other embodiments, an adhesive is not used. Those of ordinary skill in the art know of other joining methods. These are considered to be within the scope of the current invention.

In FIG. 1a, HA stepped-down portion 156 sits midway along HA distal end portion 155's length. Moreover, in this embodiment HA distal end portion 155 also serves as hub 140. The reference numbers refer to the same component because the component serves both as HA distal end 155 and as hub 140.

FIG. 1b is magnified view of shaft proximal section 106. Shaft 105 ends at shaft proximal end 112 and receives hub 140, which is either part of HA distal end 155 or not. Hub 140 can have one or more hub lumens 145—FIG. 1b shows two hub lumens 145. These hub lumens 145 extend into hub 140 longitudinally in this embodiment. But SCB catheter 100 does not need lengthwise hub lumens 145 to function correctly. Hub lumens 145 need only function to slidably and reversibly receive movable SCW end 138. FIG. 1b shows hub lumens 145 extending into hub 140 approximately three quarters of hub 140's length, but this is not critical. In some embodiments, hub lumens 145 extend completely through hub 140. Hub lumens 145 extend into hub 140 as far as or further than movable SCW end 138 extends into hub lumen 145. FIG. 1b also shows scoring wire 135 and movable SCW end 138. In this embodiment, scoring wire 135 tapers or flares outwardly after proximally exiting SCW lumen 1139. Movable SCW end 138 occupies a portion of hub lumen 145. In this embodiment, SCB catheter 100 comprises one hub lumen 145 per movable SCW end 138. But other embodiments exist in which a hub lumen can interact with more than one movable SCW end 138.

Finally, FIG. 1b shows guidewire lumen 119 passing through hub 140 and continuing into shaft 105. FIG. 1c depicts a magnified view of the region where scoring wire 135 distally exits SCW lumen 1139.

Scoring wire 135 has a path through part of SCB catheter 100. SCW lumen 1139 is a lumen that receives scoring wire 135 along some or all of shaft middle section 107 And we refer to the section of scoring wire 135 near inflatable balloon 115 as SCW IB section 137.

For discussion purposes, we begin the path at movable SCW end 138. Movable SCW end 138 resides within hub lumen 145. As we move distally along scoring wire 135, we come to the proximal end of SCW lumen 1139, which scoring wire 135 occupies. In some embodiments, scoring wire 135 tapers inwardly proximally of SCW lumen 1139. Scoring wire 135 distally exits SCW lumen 1139 at the lumen's distal end. We refer to the section of scoring wire 135 that begins at this exit as SCW IB section 137. After exiting, scoring wire 135 flares outward as it progresses distally, extending in a substantially longitudinal direction until the wire is past IB distal end 131. At that point, scoring wire 135 turns inwardly until it reaches shaft distal section 108 or GWL outer surface 121. Fixed SCW end 136 attaches to SCB catheter 100 distally of inflatable balloon 115 or at or near the point where IB distal end 131 attaches to SCB catheter 100. The portion of scoring wire 135 within SCW IB section 137 has a longitudinal region along inflatable balloon 115. The distance this longitudinal section extends from SCB catheter 100's central axis (wire distance) can have a variety of values. The distance that IB outer surface 132 extends from the central axis when inflatable balloon 115 inflates is the balloon inflation distance. Typically, the ratio of the wire distance to the balloon inflation distance or (wire distance)/(balloon inflation distance) is within the following ranges 0.99-1.01; 0.90-1.1; 0.8-1.2; and 0.5-1.5.

In the operation of the group of embodiments represented by the device in FIG. 1a, a physician places inflatable balloon 115 as described above. The physician inflates inflatable balloon 115 through HA IB lumen port 153. Balloon inflation first applies outward pressure on scoring wires 135 and then onto the lesion. Without wishing to be bound by any particular theory of operation, we believe that because movable SCW end 138 is moveably connected, scoring wire 135 does not contribute to balloon or balloon deformation caused by inflation or overinflation. Since the wire can move outwardly, it does not significantly cage the balloon. The caging effect will prevent the balloon from expanding past the wires. But if inflation continues, some other portion of the balloon will deform from the pressure exerted by the inflation fluid. In some cases, balloon deformation leads to problems with later deflating the balloon. Instead, the outwardly directed inflation pressure on scoring wire 135 causes movable SCW end 138 to move distally, which lowers the counterforce that scoring wire 135 exerts against inflatable balloon 115. As movable SCW end 138 moves distally, it recedes from hub lumen 145. In some embodiments, inflation pressure causes movable SCW end 138 to pull out of hub lumen 145. In other embodiments, movable SCW end 138 remains inside of hub lumen 145.

The physician maintains pressure in inflatable balloon 115 long enough for scoring wire 135 to have the effect the physician desires. Afterward, the physician releases pressure, inflatable balloon 115 deflates, and movable SCW end 138 re-extends into hub lumen 145.

FIGS. 2a through 2c depict different embodiments of SCB catheter 100. These embodiments are similar to those shown in FIGS. 1a through 1c. The main difference between the sets of embodiments lies in the hub and the proximal scoring wire geometry.

FIG. 2b depicts a hub 140 that has hub distal section 241 and hub proximal section 242. Hub proximal section 242 through HA stepped-down portion 156 serves to connect shaft 105 with handle assembly 150. Additionally, hub proximal section 242 serves as a stop for spring 200. Spring 200 comprises spring wire 201—the figure depicts spring wire 201 in cross-section. Spring 200 adds resilience to the mechanism of scoring wire 135.

Hub distal section 241 lies next to the distal end of spring 200. Hub distal section 241 connects (attaches) to movable SCW end 138. In some embodiments, hub distal section 241 is fixed to movable SCW end 138. In other embodiments, hub distal section 241 comprises hub lumens 145, which in some cases are fixed to movable SCW end 138. Movable SCW end 138 flares outwardly as it reaches hub distal section 241. On the other hand, the embodiment shown in FIG. 3a through 3c comprise movable SCW ends 138 that do not flare as it reaches hub distal section 241.

In the operation of the group of embodiments represented by the devices disclosed in FIGS. 1a-6, a physician places inflatable balloon 115 as described above. The physician inflates inflatable balloon 115 through HA IB lumen port 153, which first applies outer pressure on scoring wires 135 and then on the lesion. The difference in operation between the above embodiments and the group of embodiments represented by FIGS. 1a-3c is in the mechanism that that allows movement by movable SCW end 138. As in the above embodiments, in these embodiments, as inflatable balloon 115 inflates, the counterforce that scoring wire 135 would otherwise apply, is moderated by movable SCW end 138. In this group, movable SCW end 138 recedes distally as before, but hub distal section 241 also moves distally. The arrangement of hub distal section 241, spring 200, and hub proximal section 242 imparts force, through hub distal section 241, to movable SCW end 138. This force tends to proximally bias movable SCW end 138. And when the physician deflates the balloon as before, movable SCW end 138 moves proximally, substantially back to its initial position, aided by the force of spring 200.

FIGS. 4a-4c depict another embodiment of SCB catheter 100. The device of this embodiment is substantially similar to the embodiments described above. The main difference is that this version of hub distal section 241, although similar to hub distal sections described above, has narrowed region 340 that extends proximally from hub distal section 241. Narrowed region 340 sits inside of spring 200.

Similarly, FIGS. 5a-5c has narrowed region 340 and additionally has extension 451 sitting between hub distal section 241 and narrowed region 340. Finger grip 400 sits on extension 451, extending through the side of shaft proximal section 106. Finger grip 400 provides the physician some control of distal hub 450, which enables more direct control of movable SCW end 138 in these types of embodiments.

FIG. 6 discloses an embodiment of the proximal section of the device. In this embodiment, a spring 200 sits within the distal end of HA 150 and extends distally from HA 150. Hub 140 connects to HA 150 and forms a monolithic structure with HA 150. Spring 200 receives shaft proximal section 106. Movable SCW end 138 exits scoring wire lumen 1139 near the distal end of shaft proximal section 106. Movable SCW end 138 connects directly to spring 200 through any suitable method, such as soldering, welding, overmolding, gluing, or press fitting using plastic tubing. In some embodiments, movable SCW end 138 connects directly to spring 200 through a weld joint 1362. In this or other embodiments, hub cover 700 sits over hub 140 and shaft 105. In some cases, hub cover 700 provides strain relieve for the connection between HA 150 and shaft 105.

The spring 200 provides longitudinal movement and a biasing force to movable SCW end 138. When movable SCW end 138 experiences a distally directed force that moves it distally, the movement holds that away from HA 150. The restoring force or force counter to that distal stretching (counterforce) tends to move movable SCW end 138 substantially back into place once the distally directed force disappears.

FIG. 7a depicts section AA of FIG. 1a. It shows two scoring wires 135, inflatable balloon 115, IB lumen 133, and guidewire lumen 119. As can be seen, section plane AA cuts through SCB catheter 100 at shaft distal section 108. The plane also cuts inflatable balloon 115; cuts scoring wire 135 at SCW IB section 137 showing SCW cross-section 505; and cuts guidewire lumen 119. FIG. 7b depicts a similar embodiment, but with three scoring wires 135.

FIG. 8a depicts section BB of FIG. 1a. It shows two SCW lumens 1139 sitting side-by-side. It also shows IB lumen 133 and GW lumen 119. SCW lumens 1139 need not adopt a side-by-side configuration, as shown in this figure, but can adopt a configuration distributed around the perimeter of shaft 105.

Figure 8B:
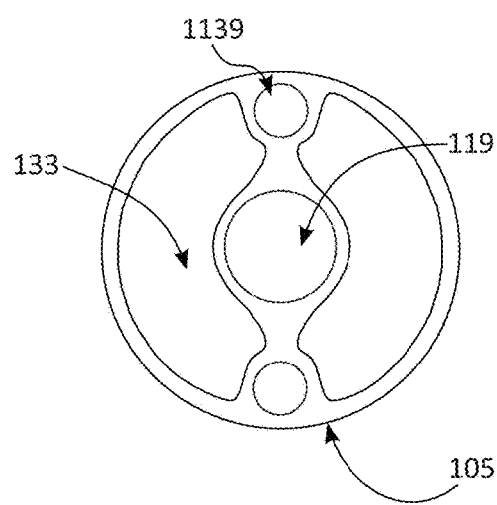
FIG. 8b is similar to FIG. 8a viewing section plane BB on a different invention embodiment.

FIG. 8b shows a different embodiment similar to FIG. 1a in cross-section. Shaft proximal section 106 is cut proximally of shaft tapered section 111. Shaft tapered section 111 tapers from shaft proximal section 106 to shaft middle section 107. Shaft 105 has shaft wall 109. For example, FIG. 8b depicts two SCW lumens 1139 distributed across from each other in shaft 105. This distribution need not be symmetric. Also in this figure, guidewire lumen 119 lies within shaft 105, and it shows SCW lumen 1139 extending longitudinally inside of shaft 105. In some embodiments, SCW lumens sit outside of the guidewire lumen.

Figure 9:
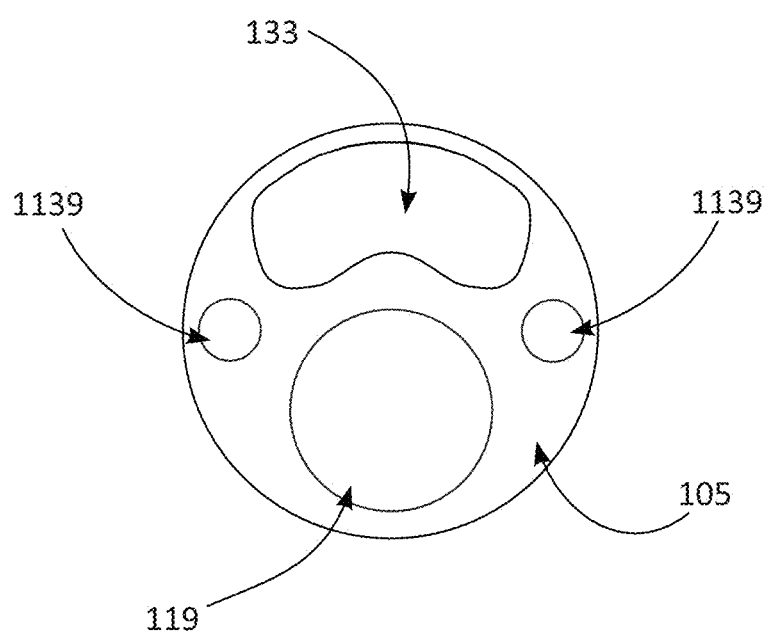
FIG. 9 is an end view of the device of FIG. 6.

FIG. 9 shows the embodiment of FIG. 6 in cross-section. In this figure, guidewire lumen 119 lies within shaft 105. In some embodiments, shaft 105 is an extrusion providing guidewire lumen 119, two SCW lumen 1139, and one lumen 133.

In any of the embodiments set out above, inflatable balloon 115 can have any of a variety of diameters ranging from 1.25-40 mm or 2.0-8.0 mm. In any of the embodiments set out above, inflatable balloon 115 can have any of a variety of lengths such as 10-300 mm or 20-300 mm. Long balloons may be particularly useful for treating peripheral lesions, which often have long diseased portions.

Some embodiments are catheters with scoring wires connected to a vibrating means to more effectively breakup hard, calcified lesions in the vasculature. In some embodiments, the scoring wires are permanently fixed to a shaft distally of the inflatable balloon, while the vibrating means connects to the proximal region of the scoring wires.

The scoring wire is fixed at the distal portion of inflatable balloon 115 and spans over the working length of inflatable balloon 115 and is connected to an external energy source proximal to inflatable balloon 115. The scoring wire enters into the catheter shaft, which can be a single or multiple lumen design. For the multiple lumen design catheter, the scoring wire may reside in a specific lumen separate from the inflation lumen. The scoring wire is connected to the external power source proximal to the working length of inflatable balloon 115. The energy source for the vibration means may reside inside the hub and can be turned on and off by the user by the press of a button. When activated, the energy source will vibrate the scoring wires at a specific frequency breaking up the hard calcified lesion. The energy source can be activated at any point during inflatable balloon 115 inflation, at the discretion of the user.

Figure 10:
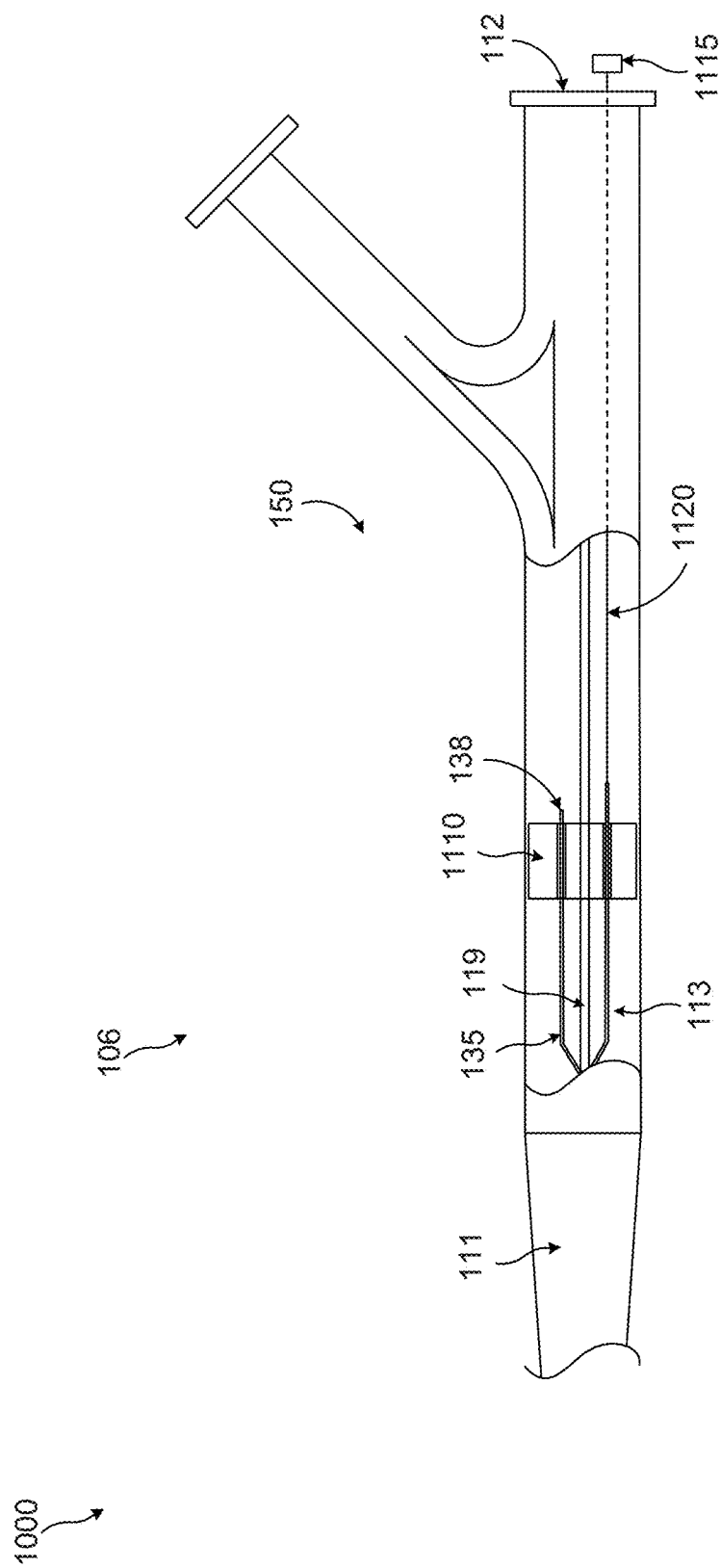
FIG. 10 is a schematic view of an invention catheter with vibration means.

FIG. 10 depicts an invention embodiment in which the balloon catheters discussed above further contain a means for vibrating scoring wires 135. This embodiment has a catheter layout similar to FIG. 1a. The figure shows a cutout view of handle assembly 150 of catheter 1000. Handle assembly 150 comprises shaft proximal section 106 that has shaft wall 109 and shaft lumen 113. Inside of shaft lumen 113 are scoring wires 135 having movable SCW ends 138, internal hub 1110, guidewire lumen 119, transmission member 1120, and shaft proximal end 112.

FIG. 10 depicts scoring wires 135 with SCW end 138 extending through internal hub 1110. Vibration means 1115 connects to movable SCW end 138 through transmission member 1120. Vibration means 1115 can be any vibration means known to those of ordinary skill in the art. Examples of vibration means 1115 include motors, micro motors, solenoids, piezoelectrics, etc.

The figures depict vibration means 1115 to be smaller than catheter 1000. On some embodiments, vibration means 1115 may be smaller than catheter 1000, the figures are not to scale; and embodiments exist in which the vibration means are larger than the catheter.

In some embodiments, hub 1110 is longitudinally movable within the lumen, and in these or other embodiments, movable SCW end 138 are bonded or not bonded to hub 1110 as desired.

Figure 11:
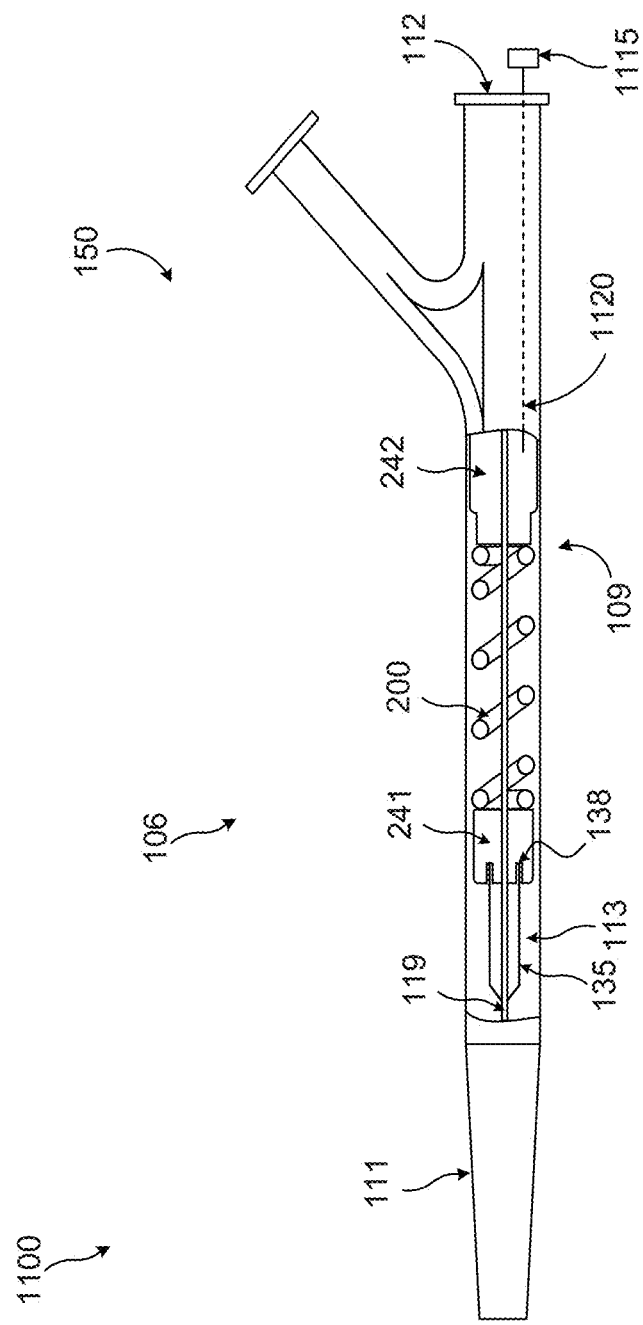
FIG. 11 is another schematic view of an invention catheter with vibration means.

Transmission member 1120 is any suitable material that one of ordinary skill in the art would find to have sufficient stiffness to transmit vibration from vibrating means 1115 to movable SCW end 138. In some embodiments, member 1120 is a rod, tube, wire etc. comprising any of the following or alloys of the following iron, nickel, chromium, molybdenum, titanium, tantalum, tungsten, steel, stainless steel, Nitinol, or their combinations. Member 1120 can also be a rod, tube, wire etc. comprising any one or any combination of metals, polymers, and ceramics FIG. 11 depicts catheter 1100 that has a balloon catheter similar to that of FIG. 2a. Handle assembly 150 comprises shaft proximal section 106 that has shaft wall 109 and shaft lumen 113. Inside of shaft lumen 113 are scoring wires 135 having movable SCW ends 138, guidewire lumen 119, transmission member 1120 and shaft proximal end 112. This embodiment has a two-piece hub with hub distal section 241 and hub proximal section 242. Transmission member 1120 connects to hub proximal section 242, which in turn contacts spring 200, which in turn contacts hub distal section 241.

In operation, the embodiments illustrated by FIGS. 10 and 11 function as follows. The balloon catheter is delivered to the treatment site. There, the operator pumps inflation fluid into inflatable balloon 115 causing it to expand. The expanded balloon pushes one or more scoring wires 135 against the lesion. At that point, the operator activates a vibration means, which vibrates transmission member 1120 and, through the connection to distal hub section 242 or movable SCW end 138, vibrates SCW 135. Thus, the vibrations transfer from the vibration means 1115 to scoring wire or wires 135 contacting the lesion. The vibrating scoring wires break up calcification and cut into the lesion. FIG. 11 depicts a two piece hub, but in some embodiments the hub is a single piece. Spring 200 may not exist in those types of embodiments. The vibrations then reach scoring wires through the connection between the single piece hub and transmission member 1120.

Figure 12:
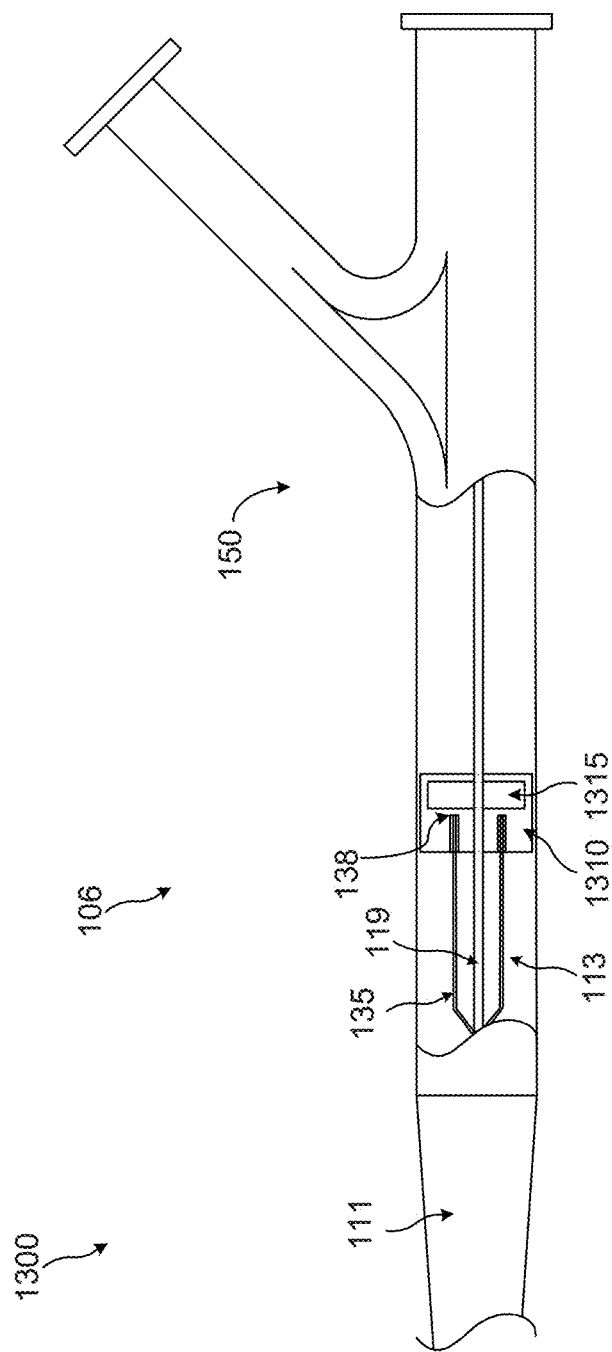
FIG. 12 is a schematic view of an invention catheter with internal vibration means.
Figure 13:
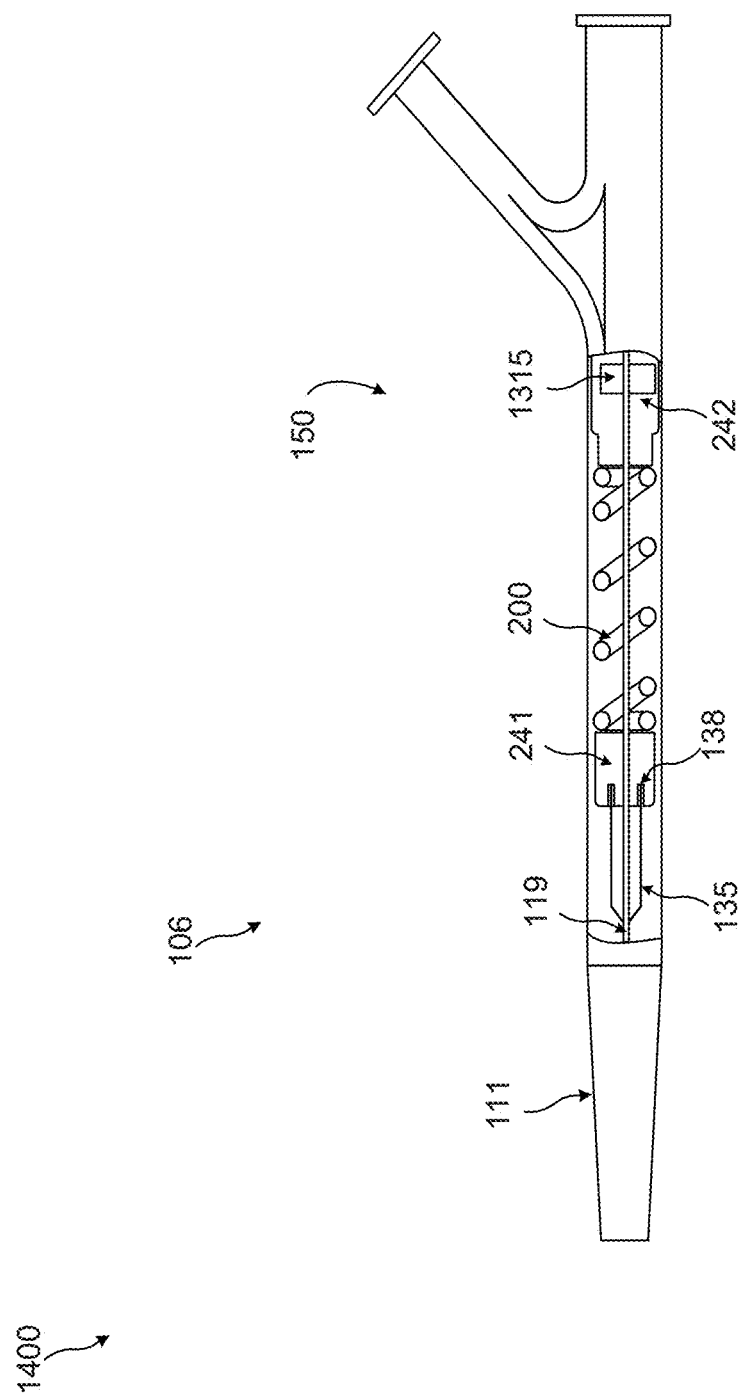
FIG. 13 is another schematic view of an invention catheter with internal vibration means.

FIGS. 12 and 13 depict a different style of vibration means. Handle assembly 150 comprises shaft proximal section 106 that has shaft wall 109 and shaft lumen 113. Inside of shaft lumen 113 are scoring wires 135 having movable SCW ends 138, guidewire lumen 119, transmission member 1120 and shaft proximal end 112. In these types of embodiments, vibration means 1315 is disposed inside of catheter 1300 and 1400 such as in vibrating hub 1310 or hub proximal section 242. In operation, the vibrations are generated inside of the catheter while the other operational aspects remain the same as above.

The embodiments illustrated by FIGS. 12 and 13 function as follows. The balloon catheter is delivered to the treatment site. There, the operator pumps inflation fluid into inflatable balloon 115 causing it to expand. The expanded balloon pushes one or more scoring wires 135 against the lesion. At that point, the operator activates a vibration means 1315, which vibrates hub 1310, hub proximal section 242, or movable SCW end 138, which vibrates SCW 135. Thus, the vibrations transfer from the vibration means 1115 to the scoring wire contacting the lesion. The vibrating scoring wires break up calcification and cut into the lesion.

Various additional embodiments of the design include, but are not limited to, the following. Scoring balloon catheter can consist of 1, 2, 3, 4, 5, or 6 longitudinal scoring wires. Shaft can consist of a triple, quadruple, quintuple, or sextuple lumen design, depending on number of scoring wires. The shaft can consist of one solid extrusion or multiple extrusions bonded together. Scoring wire can be permanently fixed to the distal portion of the balloon catheter or can be movable. Scoring wire can be connected to the external energy source at any point proximal to inflatable balloon 115 (e.g. immediately proximal to the balloon, at the hub, etc.). Scoring wires can enter the catheter shaft proximal to inflatable balloon 115 or not. Scoring wires can be directly connected to the external energy source or can be connected via a connecting component. Energy source can be built into a hub or completely external/separate from balloon catheter. Energy source can be for a single use or for multiple uses. Energy source can vibrate wires at one specific frequency or can be modulated to multiple different frequencies by the user. Hub can consist of one solid piece, as well as two or three separately molded pieces bonded together. Scoring wires can be oriented in any fashion, not only 180° apart, as illustrated. Scoring wires can have a defined diameter increase or reduction any-where along its length i.e. diameter reduction to decrease sheath profile at specific points along catheter. Exemplary embodiments can be built on an Over-The-Wire (OTX), Rapid Exchange (RX), or a Short Rapid Exchange (SRX) catheter platform. Each platform may include each of the scoring wire translating inside its own lumen. Inflatable balloon 115 or scoring wires may also have a drug layer for the prevention or reduction of neo-intimal hyperplasia.

Figure 14:
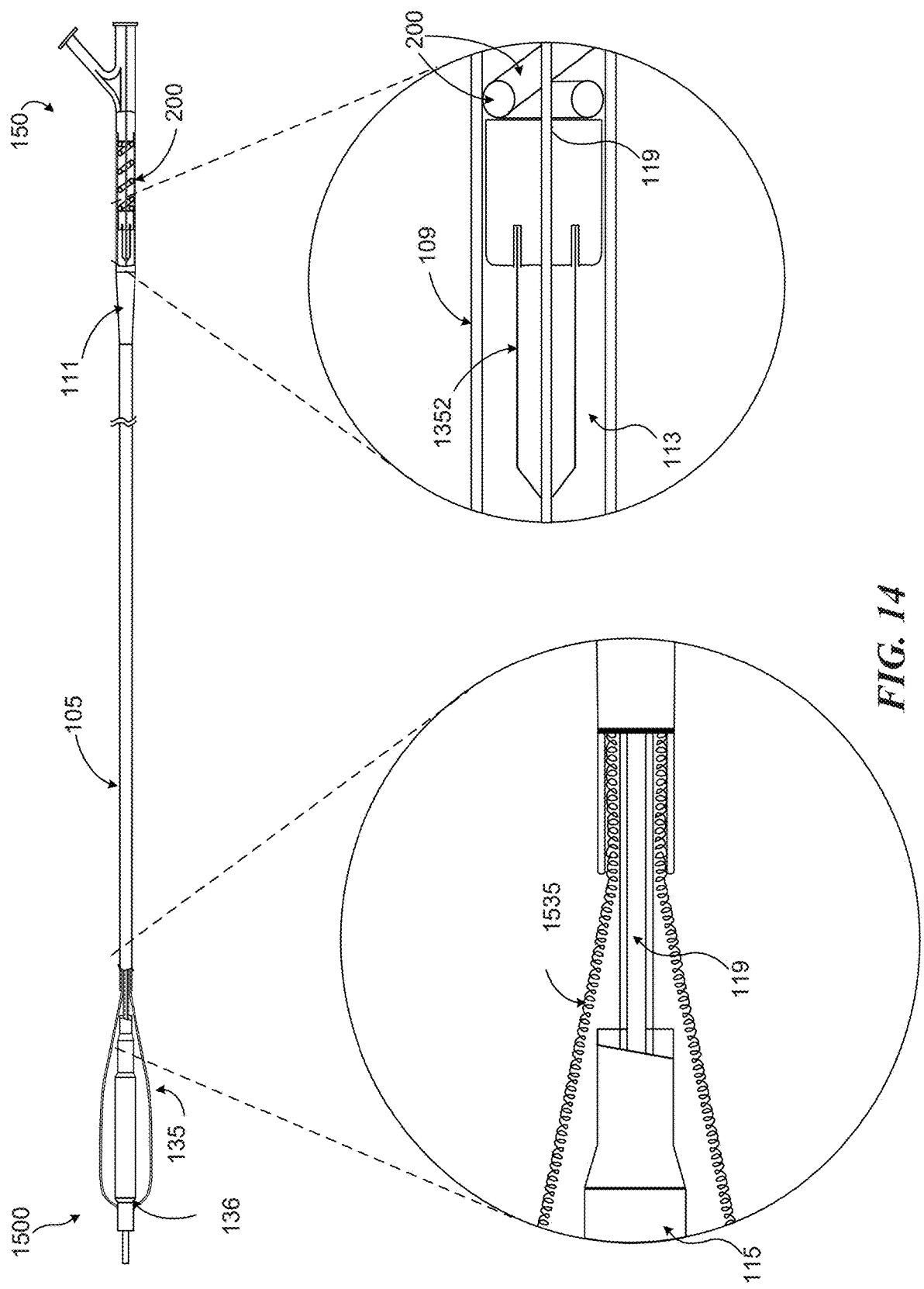
FIG. 14 is a view of an invention catheter with coiled scoring wires.

Another aspect of the invention is a balloon catheter 1500 with one or more coiled wires disposed near inflatable balloon 115 to provide focal force when dilating a calcified lesion. The coiled wire also has the ability to stretch and contract axially with inflatable balloon 115, thus reducing the likelihood of inflatable balloon 115 kinking when being inflated. For example, FIG. 14 shows this variation of balloon catheter 1500. Catheter 1500 is similar to the catheters of FIG. 2a.

FIG. 14 shows catheter 1500 with handle assembly 150, shaft 105, shaft distal section 108, inflatable balloon 115, and IB distal end 131. As discussed above, a scoring wire is disposed outside of balloon 115. In this embodiment, scoring wire 135 is replaced by a coiled wire. FIG. 14 depicts a catheter embodiment with the scoring wire coil or helical coil. SCW 135 has an outer coil diameter that depends on sheath compatibility requirements of the balloon catheter. In some embodiments, the coil diameter may range along the length of the catheter to decrease sheath profile and/or improve pushability/trackability of the device. The pitch of the helical coil may vary depending on the required sheath compatibility of the balloon catheter. In some embodiments, the coil pitch may also vary throughout the length of the balloon catheter to further aid in insertion, pushability, trackability, and withdrawal through sheath In some embodiments, the pitch of the helical coil combines with the coil and wire diameter to appear to be a solid wire to the naked eye. A diameter of the helical coil ranges from 0.009" and 0.013".

As in other scoring balloon embodiments, the SCW distal section 1351 connects to shaft 105 distally of balloon 115 and extends proximally, passing over balloon 115. In this embodiment, SCW proximal section 1352 is a straight wire. Coiled scoring wire 1535 starts from fixed scoring wire end 136 over inflatable balloon 115 to shaft 105 and dives inside of shaft 105. In this embodiment, the end of movable SCW end 138 is disposed within a distal hub 241. FIG. 14 shows coiled SCW 1535 extending along inflatable balloon 115 and into shaft 105. In this embodiment, the coiled nature transitions to a straight nature within shaft 105. In some embodiments, the scoring wire is coiled only along the balloon region. In other embodiments, the coiled nature transitions to the straight nature as coiled SCW 135 enters shaft 105.

Figure 15:
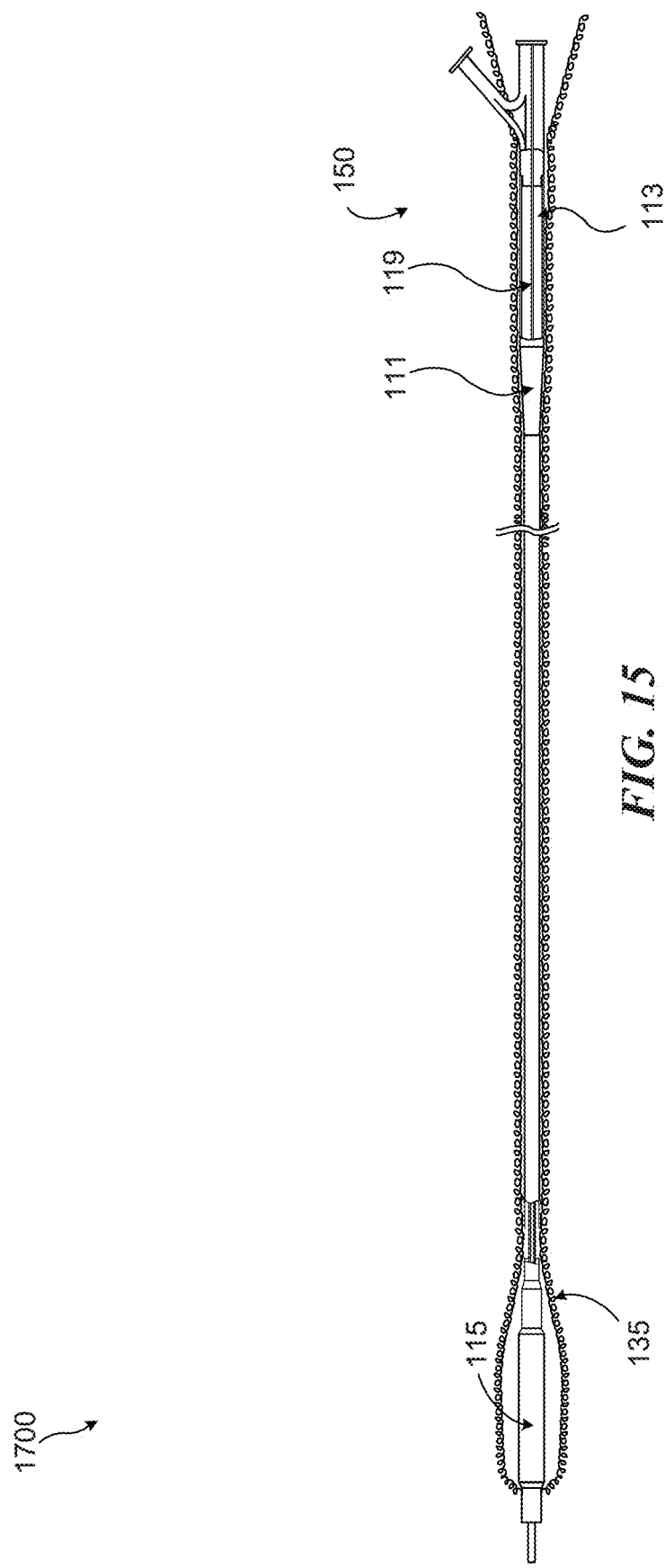
FIG. 15 is another view of an invention catheter with coiled scoring wires.

FIG. 15 shows coiled SCW 1535 as lying along the length of shaft 105. FIG. 15 shows catheter 1500 with handle assembly 150, shaft 105, shaft distal section 108, inflatable balloon 115, and IB distal end 131. As discussed above, a scoring wire runs outside of balloon 115. In this embodiment, scoring wire 135 is replaced by a coiled wire that extends along the outside of shaft 105. But in some embodiments, coiled SCW 1535 transitions to straight anywhere along shaft 105. In some embodiments, the coiled portion of coiled SCW 135 is along only the balloon region.

In operation, the catheter is placed much like the other catheters as described above. The balloon catheter 1500 is delivered to the treatment site. There, the operator pumps inflation fluid into inflatable balloon 115 causing it to expand. The expanded balloon pushes one or more scoring wires 135 against the lesion. Since the scoring wires are coiled, the inflation of inflatable balloon 115 causes coiled SCW 135 to press against and in some cases penetrate the lesion.

Upon inflation, the coiled SCW 135 becomes taut, which is brought on by the longitudinal stretching of inflatable balloon 115, and is only displaced as much as inflatable balloon 115 is stretched while it is holding its highest pressure. The coiled wire is stiff enough to penetrate plaque when the pressure of inflatable balloon 115 pushes it against the lesion. As inflatable balloon 115 deflates, the coiled section of SCW relaxes back to equilibrium. In some embodiments, there is substantially no deformation observed when coiled SCW 135 returns to equilibrium.

Shaft 105 can be an extrusion of some plastic material that is attached to handle assembly 150 on one side, and inflatable balloon 115 on the other. Shaft 105 may include a hypo-tube, and may also house a guidewire lumen as desired. Shaft 105 allows contrast, saline, or other inflation medium to be injected into inflatable balloon 115. Coiled SCW 135 can be attached to shaft 105 externally or internally.

Inflatable balloon 115 is bonded to the distal end of shaft 105. Inflatable balloon 115 neck may be bonded to the inside of the shaft 105 or the outside of the shaft 105, so long as coiled SCW 135 is able to lie near the exterior surface of inflatable balloon 115. Some sort of extrusion, such as guidewire lumen 119, or wire may run through inflatable balloon 115 to provide column strength as the physician tracks catheter 1500 to the lesion. IB distal end 131 may be sealed such that pressure remains within inflatable balloon 115 during inflation, but a guidewire is able to remain threaded through catheter 1500. Coiled SCW 135 could also be connected into the distal tip to anchor distal SCW section 1351 to the device. One or more helical or coiled wires could be attached to catheter 1500 such that the wires lie near inflatable balloon 115 and be pushed into a calcified lesion as inflatable balloon 115 is inflated. Coiled SCW 135 resembles a long tension spring.

In all of the systems described above, a coating such as a hydrophobic or hydrophilic coating may be added externally to provide ease of insertion.

Suitable drugs or therapeutic agents may also be used in conjunction with any system described above, and may include the following substances:

Antimicrobial agents may be selected, for example, from triclosan from triclosan, chlorhexidine, nitrofurazone, benzalkonium chlorides, silver salts and antibiotics such as rifampin, gentamycin and minocyclin and combinations thereof, among others.

In certain embodiments, antimicrobial agents may include triclosan, chlorhexidine and salts or combinations thereof. Anti-inflammatory agents include steroidal and non-steroidal anti-inflammatory agents. Examples of nonsteroidal anti-inflammatory drugs include aminoarylcarboxylic acid derivatives such as enfenamic acid, etofenamate, flufenamic acid, isonixin, meclofenamic acid, mefanamic acid, niflumic acid, talniflumate, terofenamate and tolfenamic acid; arylacetic acid derivatives such as acemetacin, alclofenac, amfenac, bufexamac, cinmetacin, clopirac, diclofenac sodium, etodolac, felbinac, fenclofenac, fenclorac, fenclozic acid, fentiazac, glucametacin, ibufenac, indomethacin, isofezolac, isoxepac, lonazolac, metiazinic acid, oxametacine, proglumetacin, sulindac, tiaramide, tolmetin and zomepirac; arylbutyric acid derivatives such as bumadizon, butibufen, fenbufen and xenbucin; arylcarboxylic acids such as clidanac, ketorolac and tinoridine; arylpropionic acid derivatives such as alminoprofen, benoxaprofen, bucloxic acid, carprofen, fenoprofen, flunoxaprofen, flurbiprofen, ibuprofen, ibuproxam, indoprofen, ketoprofen, loxoprofen, miroprofen, naproxen, oxaprozin, piketoprofen, pirprofen, pranoprofen, protizinic acid, suprofen and tiaprofenic acid; pyrazoles such as difenamizole and epirizole; pyrazolones such as apazone, benzpiperylon, feprazone, mofebutazone, morazone, oxyphenbutazone, phenybutazone, pipebuzone, propyphenazone, ramifenazone, suxibuzone and thiazolinobutazone; salicylic acid and its derivatives such as acetaminosalol, aspirin, benorylate, bromosaligenin, calcium acetylsalicylate, diflunisal, etersalate, fendosal, gentisic acid, glycol salicylate, imidazole salicylate, lysine acetylsalicylate, mesalamine, morpholine salicylate, 1-naphthyl salicylate, olsalazine, parsalmide, phenyl acetylsalicylate, phenyl salicylate, salacetamide, salicylamine a-acetic acid, salicylsulfuric acid, salsalate and sulfasalazine; thiazinecarboxamides such as droxicam, isoxicam, piroxicam and tenoxicam; others such as Eacetamidocaproic acid, s-adenosylmethionine, 3-amino-4-hydroxybutyric acid, amixetrine, bendazac, benzydamine, bucolome, difenpiramide, ditazol, emorfazone, guaiazulene, nabumetone, nimesulide, orgotein, oxaceprol, paranyline, perisoxal, pifoxime, proquazone, proxazole and tenidap; and pharmaceutically acceptable salts thereof.

Examples of steroidal anti-inflammatory agents (glucocorticoids) include 21-acetoxyprefnenolone, alclometasone, algestone, amicinonide, beclomethasone, betamethasone, budesonide, chloroprednisone, clobetasol, clobetasone, clocortolone, cloprednol, corticosterone, cortisone, cortivazol, deflazacort, desonide, desoximetasone, dexamethasone, diflorasone, diflucortolone, difluprednate, enoxolone, fluazacort, flucloronide, flumehtasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol priopionate, halometasone, halopredone acetate, hydrocortamate, hydrocortisone, loteprednol etabonate, mazipredone, medrysone, meprednisone, methyolprednisolone, mometasone furoate, paramethasone, prednicarbate, prednisolone, prednisolone 25-diethylaminoacetate, prednisone sodium phosphate, prednisone, prednival, prednylidene, rimexolone, tixocortal, triamcinolone, triamcinolone acetonide, triamcinolone benetonide, triamcinolone hexacetonide, and pharmaceutically acceptable salts thereof.

Analgesic agents include narcotic and non-narcotic analgesics. Narcotic analgesic agents include alfentanil, allylprodine, alphaprodine, anileridine, benzylmorphine, bezitramide, buprenorphine, butorphanol, clonitazene, codeine, codeine methyl bromide, codeine phosphate, codeine sulfate, desomorphine, dextromoramide, dezocine, diampromide, dihydrocodeine, dihydrocodeinone enol acetate, dihydromorphine, dimenoxadol, dimepheptanol, dimethylthiambutene, dioxaphetyl butyrate, dipipanone, eptazocine, ethoheptazine, ethylmethlythiambutene, ethylmorphine, etonitazene, fentanyl, hydrocodone, hydromorphone, hydroxypethidine, isomethadone, ketobemidone, levorphanol, lofentanil, meperidine, meptazinol, metazocine, methadone hydrochloride, metopon, morphine, myrophine, nalbuphine, narceine, nicomorphine, norlevorphanol, normethadone, normorphine, norpipanone, opium, oxycodone, oxymorphone, papaveretum, pentazocine, phenadoxone, phenazocine, pheoperidine, piminodine, piritramide, proheptazine, promedol, properidine, propiram, propoxyphene, rumifentanil, sufentanil, tilidine, and pharmaceutically acceptable salts thereof. Non-narcotic analgesics include aceclofenac, acetaminophen, acetaminosalol, acetanilide, acetylsalicylsalicylic acid, alclofenac, alminoprofen, aloxiprin, aluminum bis(acetylsalicylate), aminochlorthenoxazin,2-amino-4-picoline, aminopropylon, aminopyrine, ammonium salicylate, amtolmetin guacil, antipyrine, antipyrine salicylate, antrafenine, apazone, aspirin, benorylate, benoxaprofen, benzpiperylon, benzydamine, bermoprofen, brofenac, p-bromoacetanilide, 5-bromosalicylic acid acetate, bucetin, bufexamac, bumadizon, butacetin, calcium acetylsalicylate, carbamazepine, carbiphene, carsalam, chloralantipyrine, chlorthenoxazin(e), choline salicylate, cinchophen, ciramadol, clometacin, cropropamide, crotethamide, dexoxadrol, difenamizole, diflunisal, dihydroxyaluminum acetylsalicylate, dipyrocetyl, dipyrone, emorfazone, enfenamic acid, epirizole, etersalate, ethenzamide, ethoxazene, etodolac, felbinac, fenoprofen, floctafenine, flufenamic acid, fluoresone, flupirtine, fluproquazone, flurbiprofen, fosfosal, gentisic acid, glafenine, ibufenac, imidazole salicylate, indomethacin, indoprofen, isofezolac, isoladol, isonixin, ketoprofen, ketorolac, plactophenetide, lefetamine, loxoprofen, lysine acetylsalicylate, magnesium acetylsalicylate, methotrimeprazine, metofoline, miroprofen, morazone, morpholine salicylate, naproxen, nefopam, nifenazone, 5' nitro-2' propoxyacetanilide, parsalmide, perisoxal, phenacetin, phenazopyridine hydrochloride, phenocoll, phenopyrazone, phenyl acetylsalicylate, phenyl salicylate, phenyramidol, pipebuzone, piperylone, prodilidine, propacetamol, propyphenazone, proxazole, quinine salicylate, ramifenazone, rimazolium metilsulfate, salacetamide, salicin, salicylamide, salicylamide a-acetic acid, salicylsulfuric acid, salsalte, salverine, simetride, sodium salicylate, sulfamipyrine, suprofen, talniflumate, tenoxicam, terofenamate, tetradrine, tinoridine, tolfenamic acid, tolpronine, tramadol, viminol, xenbucin, zomepirac, and pharmaceutically acceptable salts thereof.

Local anesthetic agents include amucaine, amolanone, amylocaine hydrochloride, benoxinate, benzocaine, betoxycaine, biphenamine, bupivacaine, butacaine, butaben, butanilicaine, butethamine, butoxycaine, carticaine, chloroprocaine hydrochloride, cocaethylene, cocaine, cyclomethycaine, dibucaine hydrochloride, dimethisoquin, dimethocaine, diperadon hydrochloride, dyclonine, ecgonidine, ecgonine, ethyl chloride, betaeucaine, euprocin, fenalcomine, fomocaine, hexylcaine hydrochloride, hydroxytetracaine, isobutyl p-aminobenzoate, leucinocaine mesylate, levoxadrol, lidocaine, mepivacaine, meprylcaine, metabutoxycaine, methyl chloride, myrtecaine, naepaine, octacaine, orthocaine, oxethazaine, parethoxycaine, phenacaine hydrochloride, phenol, piperocaine, piridocaine, polidocanol, pramoxine, prilocaine, procaine, propanocaine, proparacaine, propipocaine, propoxycaine hydrochloride, pseudococaine, pyrrocaine, ropavacaine, salicyl alcohol, tetracaine hydrochloride, tolycaine, trimecaine, zolamine, and pharmaceutically acceptable salts thereof.

Antispasmodic agents include alibendol, ambucetamide, aminopromazine, apoatropine, bevonium methyl sulfate, bietamiverine, butaverine, butropium bromide, nbutylscopolammonium bromide, caroverine, cimetropium bromide, cinnamedrine, clebopride, coniine hydrobromide, coniine hydrochloride, cyclonium iodide, difemerine, diisopromine, dioxaphetyl butyrate, diponium bromide, drofenine, emepronium bromide, ethaverine, feclemine, fenalamide, fenoverine, fenpiprane, fenpiverinium bromide, fentonium bromide, flavoxate, flopropione, gluconic acid, guaiactamine, hydramitrazine, hymecromone, leiopyrrole, mebeverine, moxaverine, nafiverine, octamylamine, octaverine, oxybutynin chloride, pentapiperide, phenamacide hydrochloride, phloroglucinol, pinaverium bromide, piperilate, pipoxolan hydrochloride, pramiverin, prifinium bromide, properidine, propivane, propyromazine, prozapine, racefemine, rociverine, spasmolytol, stilonium iodide, sultroponium, tiemonium iodide, tiquizium bromide, tiropramide, trepibutone, tricromyl, trifolium, trimebutine, n,n-1 trimethyl-3,3-diphenyl-propylamine, tropenzile, trospium chloride, xenytropium bromide, and pharmaceutically acceptable salts thereof.

In certain embodiments, therapeutic agents for reducing pain or discomfort may be selected from ketorolac and pharmaceutically acceptable salts thereof (e.g., the tromethamine salt thereof, sold under the commercial name Torado®), 4-diethylamino-2-butynylphenylcyclohexylglycolate and pharmaceutically acceptable salts thereof (e.g., 4-diethylamino-2-butynylphenylcyclohexylglycolate hydrochloride, also known as oxybutynin chloride, sold under the commercial name Ditropang®), and combinations thereof. The amount of therapeutic agent present, will depend, for example, upon the efficacy of the therapeutic agent employed, the release rate, and so forth. One skilled in the art can readily determine an appropriate therapeutic agent loading to achieve the desired outcome.

In some embodiments, the surface of IB 115 is embossed with any of a variety of patterns. For example, in some embodiments, the surface of IB 115 is embossed with a checkered pattern. Additionally, in some embodiments, inflatable balloon 115 tapers along its longitudinal direction.

In some embodiments, scoring wire 135 sits within SCW lumen 1139. And in some embodiments, SCW lumen 1139 sits outside of shaft 105.

Although the invention has been described in conjunction with specific embodiments, many alternatives, modifications, and variations will be apparent to those skilled in the art. Accordingly, it embraces all such alternatives, modifications, and variations that fall within the appended claims' spirit and scope. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

The invention claimed is:

1. A scoring balloon catheter comprising:
a shaft having a distal region and a lumen;
an inflatable balloon mounted on the distal region;
a handle assembly at least partially comprising a hub mounted in the shaft proximally of the balloon, on the proximal-most half of the shaft, or on the proximal end of the shaft wherein at least a proximal section of the hub is in a fixed longitudinal position with respect to the shaft;
a scoring wire mounted to the shaft distally of the distal end of the balloon and extending proximally past the proximal end of the balloon, wherein the scoring wire has a proximal end terminating at and disposed within the hub; and
a vibrating means connected to the scoring wire via a transmission member for vibrating the scoring wire, wherein the transmission member includes a distal end disposed within the handle assembly.

2. The catheter of claim 1 wherein the vibrating means is selected from motors, micro motors, solenoids, and piezoelectrics.

3. The catheter of claim 1, wherein the transmission member has a driven end and transmitting end, said transmitting end corresponding to the distal end of the transmission member, wherein the transmitting end contacts the hub or the proximal end of the scoring wire.

4. The catheter of claim 3 wherein the transmission member extends through the wall of the shaft.

5. The catheter of claim 4 wherein the transmission member extends distally into a proximal end of the catheter.

6. The catheter of claim 5 wherein the vibrating means imparts longitudinal motion to the scoring wire.

7. The catheter of claim 5 wherein the vibrating means imparts axial motion to the scoring wire.

8. The catheter of claim 1 wherein the vibrating means is disposed completely inside the catheter.

* * * * *